United States Patent
McKinley et al.

(10) Patent No.: US 8,862,217 B2
(45) Date of Patent: Oct. 14, 2014

(54) OPTIC FUNCTION MONITORING PROCESS AND APPARATUS

(76) Inventors: Laurence M. McKinley, Escondido, CA (US); Donald Bernstein, Rancho Santa Fe, CA (US); Ricardo Bravo, South Gate, CA (US)

(*) Notice: Subject to any disclaimer, the term of this patent is extended or adjusted under 35 U.S.C. 154(b) by 1271 days.

(21) Appl. No.: 12/500,216

(22) Filed: Jul. 9, 2009

(65) Prior Publication Data
US 2010/0056935 A1 Mar. 4, 2010

Related U.S. Application Data

(60) Provisional application No. 61/079,258, filed on Jul. 9, 2009.

(51) Int. Cl.
| | |
|---|---|
| A61B 5/04 | (2006.01) |
| A61B 5/0484 | (2006.01) |
| A61B 5/00 | (2006.01) |
| A61B 3/18 | (2006.01) |
| A61B 3/16 | (2006.01) |
| A61B 3/12 | (2006.01) |
| A61B 3/113 | (2006.01) |

(52) U.S. Cl.
CPC .......... *A61B 5/04842* (2013.01); *A61B 3/18* (2013.01); *A61B 3/16* (2013.01); *A61B 5/412* (2013.01); *A61B 5/04001* (2013.01); *A61B 5/4821* (2013.01); *A61B 3/1241* (2013.01); *A61B 3/113* (2013.01)
USPC .......................................... 600/544; 600/504

(58) Field of Classification Search
USPC ....................................................... 600/558
See application file for complete search history.

(56) References Cited

U.S. PATENT DOCUMENTS

| | | | | |
|---|---|---|---|---|
| 5,916,179 | A * | 6/1999 | Sharrock | 600/587 |
| 7,314,454 | B2 * | 1/2008 | Mallinger et al. | 600/587 |
| 2004/0243017 | A1 | 12/2004 | Causevic | |
| 2005/0200808 | A1 | 9/2005 | Wyatt | |
| 2006/0135864 | A1 | 6/2006 | Westerlund et al. | |
| 2010/0238405 | A1 * | 9/2010 | Newman et al. | 351/209 |

FOREIGN PATENT DOCUMENTS

| | | |
|---|---|---|
| WO | 0172211 A1 | 10/2001 |
| WO | 0178586 A1 | 10/2001 |

OTHER PUBLICATIONS

VEP asymmetry with ophthalmological and MRI findings in two achiasmatic children, Jelka Brecelj, Branka Stirn-Kranjc, Nuška Pečarič-Meglič, Miha Škrbec, Documenta Ophthalmologica Mar. 2007, vol. 114, Issue 2, pp. 53-65.*

(Continued)

*Primary Examiner* — Michael Kahelin
*Assistant Examiner* — Karen Toth
(74) *Attorney, Agent, or Firm* — KPPB LLP

(57) ABSTRACT

A method and apparatus for monitoring optic function is provided. The apparatus and method relies on two principle modes of measuring the function of the optic nerve, namely, monitoring VEPs for neural function, and monitoring at least one additional parameter of optic function such as intraocular pressure, blood flow or location of the eye to provide a multi-variable optic function monitor. The method and apparatus is proposed for the use to diagnose and potentially prevent the incidence of POVL and anaesthesia awareness in patients during medical procedures.

16 Claims, 12 Drawing Sheets

(56) References Cited

OTHER PUBLICATIONS

Po-Lei Lee, Jen-Chuen Hsieh, Chi-Hsun Wu, Kuo-Kai Shyu, Yu-Te Wu, Brain computer interface using flash onset and offset visual evoked potentials, Clinical Neurophysiology, vol. 119, Issue 3, Mar. 2008, pp. 605-616, ISSN 1388-2457, http://dx.doi.org/10.1016/j.clinph.2007.11.013. (http://www.sciencedirect.com/science/article/pii/S138824570700662.*

Marks et al., "Blindness Following Bilateral Radical Neck Dissection", Head & Neck, Jul./Aug. 1990, vol. 12, pp. 342-345.

McKinley et al., "Clinical Experience with Spinal Cord Monitoring in Spinal Injury Patients", The Journal of Neurological and Orthopaedic Surgery, Apr. 1982, vol. 3, Issue 1, pp. 1-5.

Myers et al., "Visual loss as a complication of spine surgery (abstract)", Spine, 1997, vol. 22, No. 12, 3 pgs.

Nawa et al., "Bilateral posterior optic neuropathy after bilateral radical net dissection and hypotension", Graefe's Arch. Clin. Exp. Ophthalmol, 1992, vol. 230, pp. 301-308.

Ota et al., "Intraoperative monitoring of cortically recorded visual response for posterior visual pathway", J. Neurosurg. 2010, vol. 112, pp. 285-294.

Ozcan et al., "The Effect of Body Inclination During Prone Positioning on Intraocular Pressure in Awake Volunteers: A Comparison of Two Operating Tables", Anesth. Analg., 2004, vol. 99, pp. 1152-1158.

Petrig et al., "Laser Doppler Flowmetry and Optic Nerve Head Blood Flow", American Journal of Ophthalmology, Apr. 1999, vol. 127, No. 4, pp. 413-425.

Posner, "Committee on Professional Liability Forms a New Registry to Investigate Postoperative Blindness", ASA Newsletter, Oct. 1999, vol. 63, 2 pgs.

Roth et al., "Eye Injuries After Nonocular Surgery: A Study of 60,965 Anesthetics from 1988 to 1992", Anesthesiology, Nov. 1996, vol. 85, Issue 5, pp. 1-12.

Roth et al., "Visual Loss in a Prone-Positioned Spine Surgery Patient with the Head on a Foam Headrest and Goggles Covering the Eyes: An Old Complication with a New Mechanism", Anesth. Analg., 2007, vol. 104, pp. 1185-1187.

Sadda et al., "Clinical Spectrum of Posterior Ischemic Optic Neuropathy", American Journal of Opthamology, Nov. 2001, vol. 132, pp. 743-750.

Sasaki et al., "Intraoperative monitoring of visual evoked potential: introduction of a clinically useful method", J. Neurosurg. 2010, vol. 112, pp. 273-284.

Schobel et al., "Posterior ischemic optic neuropathy following bilateral radical neck dissection", Int. J. Oral Maxilloffac. Surg., 1995, vol. 24, pp. 283-287.

Shaw et al., "Age-Dependent Changes in the Latency of the Pattern Visual Evoked Potential", Electroencephalography and Clinical Neurophysiology, 1980, vol. 48, pp. 237-241.

Stambough et al., "Ophthalmologic Complications Associated with Prone Positioning in Spine Surgery", Journal of the American Academy of Orthopaedic Surgeons, 2007, vol. 15, pp. 156-165.

Stevens et al., "Ophthalmic Complications After Spinal Surgery", Spine, 1997, vol. 22, No. 12, pp. 1319-1324.

Uhl et al., "Effect of Halothane Anesthesia on the Human Cortical Visual Evoked Response", The Journal of Anesthesiology, Oct. 1980, vol. 53, No. 4, pp. 273-276.

Valencia et al., "Overview: Spinal Cord Monitoring", The Journal of Neurological and Orthopaedic Surgery, Apr. 1982, vol. 3, Issue 1, pp. 11-17.

Valencia et al., "Spinal Evoked Potentials, Cord Distraction and Functional Studies in Animals", The Journal of Neurological and Orthopaedic Surgery, Apr. 1982, vol. 3, Issue 1, pp. 6-10.

Warner et al., "Practice Advisory for Perioperative Visual Loss Associated with Spine Surgery", Anesthesiology, 2006, vol. 104, pp. 1319-1328.

Warner et al., "The Frequency of Perioperative Vision Loss", Anesthesia and Analgesia, Dec. 2001, vol. 93, Issue 6, pp. 1-9.

West et al., "Loss of vision in one eye following scoliosis surgery", British Journal of Ophthalmology, 1990, vol. 74, pp. 243-244.

Williams, "Postoperative blindness", Anesthesiology Clin. N. Am., 2002, vol. 20, pp. 605-622.

Wirtschafter et al., "Intraocular axonal swelling produced by partial, immediately retrobulbar ligature of optic nerve", Invest. Ophthalmol. Visual Sci., Jun. 1977, pp. 537-541.

Wolfe et al., "Unilateral Blindness as a Complication of Patient Positioning for Spinal Surgery", Spine, 1992, vol. 17, No. 5, pp. 600-605.

Yanagidate, "Corneal abrasion after the wake-up test in spinal surgery", J. Anesth. Jan. 1, 2003, vol. 17, No. 3, 1 pg.

International Search Report for International Application PCT/US2009/050123, Report completed Aug. 24, 2009, 4 pgs.

Written Opinion for International Application No. PCT/US2009/050123, Opinion completed Aug. 24, 2009, 11 pgs.

Alexandrakis et al., "Bilateral Posterior Ischemic Optic Neuropathy After Spinal Surgery", American Journal of Ophthalmology, Mar. 1999, vol. 127, No. 3. pp. 354-355.

Allison et al., "Development and Aging Changes in Somatosensory, Auditory and Visual Evoke Potentials", Electroencephalography and Clinical Neurophysiology, 1984, vol. 58, pp. 14-24.

Baig et al., "Vision loss after spine surgery: review of the literature and recommendations", Neurosurg. Focus, 2007, vol. 23, No. 5, pp. 1-9.

Boehm et al., "The Effect of Age on Optic Nerve Head Blood Flow", Investigative Ophthalmology & Visual Science, Apr. 2005, vol. 46, No. 4, pp. 1291-1295.

Brown et al., "Anemia and Hypotension as Contributors to Perioperative Loss of Vision", Anesthesiology, 1994, vol. 80, No. 1, pp. 222-226.

Buono et al., "Perioperative Posterior Ischemic Optic Neuropathy: Review of the Literature", Survey of Ophthalmology, Jan.-Feb. 2005, vol. 50, No. 1, pp. 15-26.

Cedzich et al., "Factors that limit the use of flash visual evoked potentials for surgical monitoring", Electroencephalography and Clinical Neurophysiology, 1988, vol. 71, pp. 142-145.

Celesia et al., "Cortical blindness and residual vision: Is the "second" visual system in humans capable of more than rudimentary visual perception?", Neurology, Jun. 1991, vol. 41, pp. 862-868.

Celesia et al., "Visual Evoked Potentials: A Practical Approach Within the Guidelines for Clinical Evoked Potential Studies", Am. J. EEG Technol., 1985, vol. 25, pp. 93-113.

Cheng et al., "The Effect of Prone Positioning on Intraocular Pressure in Anesthetized Patients", Anesthesiology, 2001, vol. 95, pp. 1351-1355.

Chi et al., "Effects of Fentanyl Anesthesia on Visual Evoked Potentials in Humans", Anesthesiology, 1987, vol. 67, pp. 827-830.

Dolman et al., "Aging of the Optic Nerve", Arch. Ophthalmol., Nov. 1980, vol. 98, pp. 2053-2058.

Dorfman et al., "Age-related changes in peripheral and central nerve conduction in man", Neurology, Jan. 1979, vol. 29, pp. 38-44.

Dunker et al., "Perioperative Risk Factors for Posterior Ischemic Optic Neuropathy", J. Am. Coll. Surg., 2002, vol. 194, p. 705-710.

Frost, "He Can't Be Blind: It Was Only Back Surgery", Current Reviews in Clinical Anesthesia, Feb. 8, 2007, Lesson 14, vol. 14, Cover Page, pp. 167-173.

Gill et al., "Postoperative visual loss associated with spinal surgery", Eur. Spine J. 2006, vol. 15, pp. 479-484.

Hayreh, "Blood Flow in the Optic Nerve Head and Factors that May Influence it", Progress in Retinal and Eye Research, 2001, vol. 20, No. 5, pp. 595-624.

Hayreh, "The Blood Supply of the Optic Nerve Head and the Evaluation of It—Myth and Reality", Progress in Retinal and Eye Research, 2001, vol. 20, No. 5, pp. 563-593.

Ho et al., "Ischemic Optic Neuropathy Following Spine Surgery", J. Neurosurg. Anesthesiol., 2005, vol. 17, pp. 38-44.

Huber, "Bilateral cortical blindness after lumbar spine surgery. A case report", Spine, Aug. 15, 1998, vol. 23, No. 16, pp. 1807-1809.

Hunt et al., "Changes in Intraocular Pressure in Anesthetized Prone Patients", J. Neurosurg. Anesthesiol., 2004, vol. 16, pp. 287-290.

(56) References Cited

OTHER PUBLICATIONS

Johnson et al., "Bilateral Retrobulbar Optic Nerve Infarctions After Blood Loss and Hypotension", Ophthalmology, Dec. 1987, vol. 94, No. 12, pp. 1577-1584.

Kamming et al., "Postoperative visual loss following prone spinal surgery", British Journal of Anaesthesia, 2005, vol. 95, No. 2, pp. 257-260.

Katz et al., "Visual Field Defect After Posterior Spine Fusion", Spine, 2005, vol. 30, No. 3, pp. E83-E85.

Kawasaki et al., "Recovery of postoperative visual loss following treatment of severe anaemia", Clinical & Experimental Opth., 2006, vol. 34, No. 5, pp. 497-499.

Krauss et al., "Autoenucleation", Survey of Ophthalmology, Nov.-Dec. 1984, vol. 29, No. 3, pp. 179-187.

Kumar et al., "Blindness and Rectus Muscle Damage Following Spinal Surgery", Brief Reports, American Journal of Ophthalmology, Nov. 2004, vol. 138, No. 5, pp. 889-891.

Lampert et al., "Pathology of the optic nerve in experimental acute glaucoma", Investigative Ophthalmology, Apr. 1988, vol. 7, No. 2, pp. 199-213.

Lauer, "Visual Loss After Spine Surgery", J. Neurosurg. Anesthesiol., Jan. 2004, vol. 16, No. 1, pp. 77-79.

Lee, "Blind Spot", Surgery/Anesthesia, Jun. 2005, pp. 1-10.

Lee et al., "The American Society of Anesthesiologists Postoperative Visual Loss Registry", Anesthesiology, 2006, vol. 105, pp. 652-659.

Nogawa et al., "Changes in the Latency of the Maximum Positive Peak of Visual Evoked Potential During Anesthesia", Arch. Jpn. Chir., May 1991, vol. 60, No. 3, pp. 143-153.

Freye, "Cerebral monitoring in the operating room and the intensive care unit-an introductory for the clinician and a guide for the novice wanting to open a window to the brain", Journal of Clinical Monitoring and Computing, vol. 19, 2005, pp. 77-168, XP002690653, p. 144-164.

\* cited by examiner

OPTIC FUNCTION MONITORING PROCESS AND APPARATUS

CROSS-REFERENCE TO RELATED APPLICATIONS

The current application claims priority to U.S. Provisional Application No. 61/079,258, filed Jul. 9, 2009, the disclosure of which is incorporated herein by reference.

FIELD OF THE INVENTION

The invention is directed to a method and apparatus for monitoring optic function in consciousness-altered patients; and more particularly to method and apparatus for the real-time monitoring of optic function for evaluating potential optic damage or unintended interoperative awareness.

BACKGROUND OF THE INVENTION

The use of some form of anesthesia, or "reversible lack of awareness", can be dated as far back as the Greek and the Persian empires. However, it was not until the $19^{th}$ century that modern narcotic anesthesia agents would be discovered. The introduction and the development of effective anesthetics in the 19th century was, with Listerian techniques, one of the keys to the development of successful surgical protocols.

Although anesthesia has made modern surgical procedures possible the process has, from the beginning, been fraught with danger. For example, the first chloroform surgeries were performed in late 1847, and the first fatality directly attributed to chloroform anesthesia was recorded mere months later in January 1848. The framed physician John Snow published a classical study of chloroform deaths as early as 1858. Indeed, medical literature is replete with the names of prominent figures in medicine that wrote about the dangers of anesthesia. Harvey Cushing, generally considered the father of modern neurosurgery, lost a patient who aspirated gastric contents during ether anesthetic. He later wrote that this event almost caused him to leave medical school. As a result, anesthesiologists the world over have long been concerned with and involved in studies related to anesthesia safety. Many prominent anesthesiologists in the United States began to collect statistics of anesthetic morbidity and mortality as early as the 1930's. However, the dangers of anesthesia are not purely historical. Indeed, it was not until 1983 that a modern system of reporting was implemented so that anesthesiologists could develop statistics and define the parameters of future studies.

The results of these studies have been to create standards and protocols for how anesthesia is administered and how a patient is monitored while under anesthesia. For example, under current protocols patients being treated under general anesthetics must be monitored continuously to ensure the patient's safety. For minor surgery, this generally includes monitoring of heart rate (via ECG or pulse oximetry), oxygen saturation (via pulse oximetry), non-invasive blood pressure, inspired and expired gases (for oxygen, carbon dioxide, nitrous oxide, and volatile agents). For moderate to major surgery, monitoring may also include temperature, urine output, invasive blood measurements (arterial blood pressure, central venous pressure), pulmonary artery pressure and pulmonary artery occlusion pressure, cerebral activity (via EEG analysis), neuromuscular function (via peripheral nerve stimulation monitoring), and cardiac output. In addition, the operating room's environment must be monitored for temperature and humidity and for buildup of exhaled inhalational anesthetics, which might impair the health of operating room personnel. While these protocols have resulted in significant improvements in anesthesia related mortality, they have not eliminated all of the risks associated with anesthetized and otherwise consciousness altered individuals.

For example, one risk that has become more prevalent over time is perioperative visual loss. Perioperative visual loss (POVL) broadly refers to permanent impairment or total loss of sight associated with general anesthesia. The relevant perioperative period generally includes a time from the immediate preoperative assessment through discharge from the acute healthcare facility, and is indicated for patients who, within seven days following non-opthalmological surgery, began to develop visual impairment and/or blindness. Despite the data and the in-depth demographic studies available, the mechanism of perioperative ischemic optic neuropathy is still theoretical and, thus, up until this time, monitoring and prevention strategies could not be effectively defined.

Another potentially disturbing complication can be 'anesthesia awareness'. In this situation, patients paralyzed with muscle relaxants may awaken during their anesthesia, due to decrease in the levels of drugs providing sedation, lack of awareness and/or pain relief. If the anesthesia provider misses this fact, the patient may be aware of his surroundings, but be incapable of moving or communicating that fact.

Neurological monitors are becoming increasingly available which may help decrease the incidence of POVL and awareness. One exemplary monitor that is currently available is the BIS monitor, manufactured by Aspect Medical Systems of Natick, Mass. The BIS device monitors EEG-based brain function to reduce the incidence of recall or awareness of a patient while under anesthesia. During function the BIS monitor uses proprietary algorithms to monitor brain activity and give the anesthesiologist a series of empiric numbers upon which to assess the patient's level of consciousness. While monitoring EEG-based brain activity has been shown to be of some benefit in allowing for quicker recovery from anesthesia, studies have indicated that the EEG measurements can be dramatically impacted even when the patient is not under anesthesia. For example, in a study published in 2008 it was shown that BIS scores could be changed by as much as 20 basis points simply by the administration of muscle relaxants to non-anesthetized patients. (Lu, et al., Int. Anesthesia Res. Soc., 107:4, 2008, the disclosure of which is incorporated herein by reference.) Likewise, a study published in the New England Journal of Medicine showed that awareness under anesthesia occurred in patients even when the BIS values were within target ranges. (Avidan, M. S., et al., New England Journal of Medicine, 358, 1097, 2008, the disclosure of which is incorporated herein by reference.)

A second device being marketed for use as an anesthesia monitor is the BAER system, which stands for Brain Auditory Evoked Response. These monitors have been used successfully in the past to evaluate brain injury; however, recently it has been suggested that such a technique could be used to monitor the depth of anesthesia. Recent studies have openly questioned this assumption. However, some studies on the efficacy of the system have shown that there is no correlation between the potentials measured by the BAER system and level of anesthesia.

In summary, despite the widespread marketing of these new monitoring devices many case reports exist in which awareness under anesthesia has occurred despite apparently adequate anesthesia as measured by such neurologic monitors. Accordingly, a method and apparatus for monitoring a patient under anesthesia that could provide better data concerning both POVL and Anesthesia Awareness is needed to provide surgeons with adequate information to enable real-time prevention of these serious conditions.

SUMMARY OF THE INVENTION

The current invention is directed to a method and apparatus for monitoring in real-time optic nerve function for use in consciousness-altered individuals.

In one embodiment, the method/apparatus includes the placement of at least one optic function sensor proximate to the eye that is designed to stimulate and monitor the function of at least one of the optic nerve or the optic cortex. In such an embodiment, the at least one optic function sensor may stimulate the eye by producing a visual evoked potential in at least one of the nasal or temporal halves of the optic nerve, such as by a light emitting diode or other suitable mechanism.

In another embodiment, the method/apparatus includes the placement of at least one pressure sensor proximate to the eye that is designed to monitor the intraocular pressure of the eye. In such an embodiment the pressure sensor may be a tonometer.

In yet another embodiment, the method/apparatus includes the placement of a blood flow sensor proximate to the eye that is designed to monitor one of either retinal or optic blood flow. In such an embodiment, the blood flow sensor may be selected from one of either a near-infrared spectrometer or a laser Doppler velocimeter.

In still another embodiment, the one or more of the above sensors are integrated into a sensor band. In such an embodiment the sensor band may be incorporated into an eye-cover.

In still yet another embodiment, the eye-cover may take the form of a pair of goggles.

In still yet another embodiment, the method/apparatus of the current invention further includes analyzing the output from the visual evoked potential curves using one of the following mathematical formulas:

$AI\text{-}1 = P2/TL1$ in ($\mu$V/ms)

$AI\text{-}2 = (AI\text{-}1)^n$ in ($\mu$V/ms)

$AI\text{-}3 = (P2)^x/(TL1)^y$ in ($\mu$V/ms)

$AI\text{-}4 = (AI\text{-}3)^n$ in ($\mu$V/ms)

$AI\text{-}5 = (\delta(EVP2)/\delta t_{max})/TL1$ in ($\mu$V/ms)

$AI\text{-}6 = (\delta(EVP2)/\delta t_{max})^x/(TL1)^y$ in ($\mu$V/ms)

$AI\text{-}7 = AI\text{-}6^n$ in ($\mu$V/ms)

$AI\text{-}8 = (\delta(EVP2)/\delta t_{mean})/TL1$ in ($\mu$V/ms)

$AI\text{-}9 = (\delta(EVP2)/\delta t_{mean})^x/(TL1)^y$ in ($\mu$V/ms)

$AI\text{-}10 = (\delta(EVP2)/\delta t_{mean})^x/(t_1^y/P2^z)^m$ in ($\mu$V/ms)

$AI\text{-}11 = AI\text{-}10^n$ in ($\mu$V/ms)

$AI\text{-}12 = \delta(EVP2)/\delta t_{max}/t_1/P2$ in ($\mu$V$^2$/ms$^2$)

$AI\text{-}13 = (\delta(EVP2)/\delta t_{max})^x/t_1^y/P2^z$ in ($\mu$V$^2$/ms$^2$)

$AI\text{-}14 = (\delta(EVP2)/\delta t_{mean})^x/(t_1^y/P2^z)^m$ in ($\mu$V$^2$/ms$^2$)

$AI\text{-}15 = AI\text{-}14^n$ in ($\mu$V/ms)

$AI\text{-}16 = (\delta(EVP2)/\delta t_{max})^x/(t_1^y/P2^z)^m$ in ($\mu$V$^2$/ms$^2$)

$AI\text{-}17 = AI\text{-}16^n$ in ($\mu$V/ms)

$AI\text{-}D = ((AI\text{-}1) \cdot (AI\text{-}17)/(CV(AI\text{-}1) \cdot CV(AI\text{-}17)))$ wherein in each of the above equations the exponents have a value from 0.333 to 3 and preferably from 0.5 to 2.

BRIEF DESCRIPTION OF THE DRAWINGS

The description will be more fully understood with reference to the following figures and data graphs, which are presented as exemplary embodiments of the invention and should not be construed as a complete recitation of the scope of the invention, wherein.

DETAILED DESCRIPTION OF THE INVENTION

The current invention is directed to a method and apparatus for the real-time monitoring of optic nerve function. The invention recognizes that although great advance have been made in preventing fatalities in consciousness altered patients, it is very difficult to accurately monitor the more subtle ongoing stresses that can occur in consciousness altered individuals, such as those under anesthesia, and that as such a need exists for a monitoring system that can accurately monitor, and potentially prevent injury by providing data on the function of a patient's optic nerve. For example, the method and apparatus of the current invention would allow a surgical team to monitor the function of the optical nerve in real-time during surgery, thereby providing information on the status of the patient. In addition, the current invention specifically recognizes that the function of the optic nerve can be used as a diagnostic tool for common anesthesia induced injuries, including, for example, POVL and anesthesia awareness.

The method and device of the current invention is able to monitor such function for two principal reasons. First, unlike conventional monitors, such as BIS, which monitor activity in only a portion of the brain (the cerebrum for BIS and the midbrain for BAER), the device and method of the current invention monitors activity in multiple parts of the brain simultaneously. Specifically, because it examines visual evoked potentials, the current technique must look at activity across three neurological systems—the peripheral nerves, the midbrain and the cortex. This is because visual evoked potentials are impacted by the function optic nerve (a peripheral nerve) and also the optic chiasma (a midbrain structure). Second, current techniques are designed to watch physiological variables and look for stability and constancy. The current invention is designed to watch for change in neurological activity, and more particularly to watch for a trend of change indicative of an impending adverse event.

Figure 1:
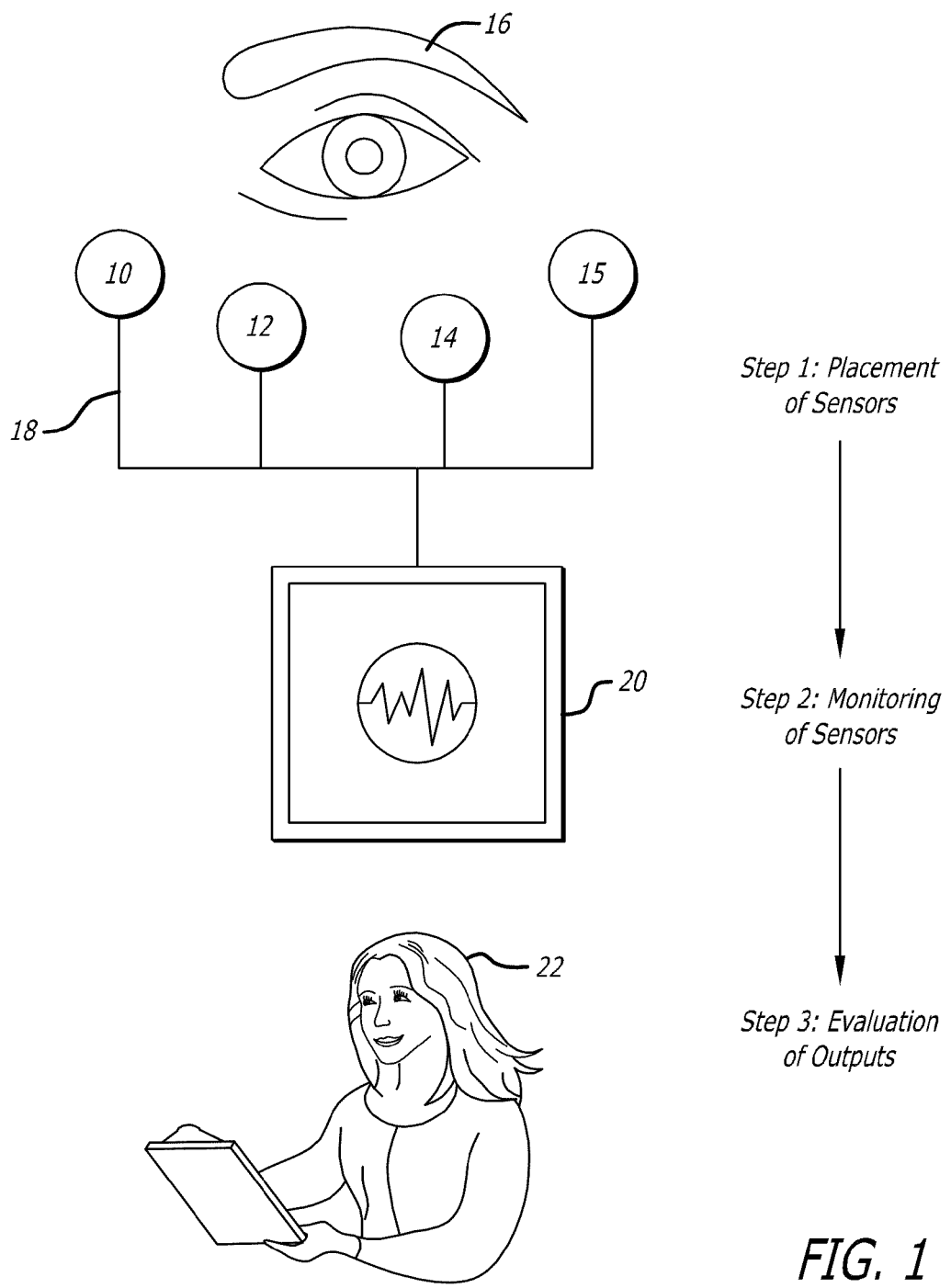
FIG. 1 provides a schematic of an exemplary embodiment of the method and apparatus of current invention.

As discussed above, in one embodiment the current invention is directed to a method/apparatus for monitoring optic nerve function. FIG. 1 provides a schematic diagram of the proposed apparatus in combination with a flowchart showing the method of the current invention. As shown, in one embodiment the optic nerve function monitoring method/apparatus of the current invention comprises the placement and monitoring of at least a sensor capable of providing information on the function of the optic nerve and optic cortex via visual evoked potentials (10), and optionally at least one of three additional optic nerve sensors: a sensor for monitoring the intraocular pressure of the eye (12), a sensor for monitoring retinal blood flow (14), and a sensor for measuring the location and movement of the eye (15). A description of each of the sensors and their function in monitoring optic nerve function is provided below. In general though the sensors (10, 12, 14, 15) are placed either individually or together against the closed lid of the patient's eye (16). Leads (18) connect the sensors (10, 12, 14, 15) to a remote monitor (20) that can communicate the signal information to a trained physician (22) for evaluation.

Visual Evoked Potential Sensor

Figure 2:
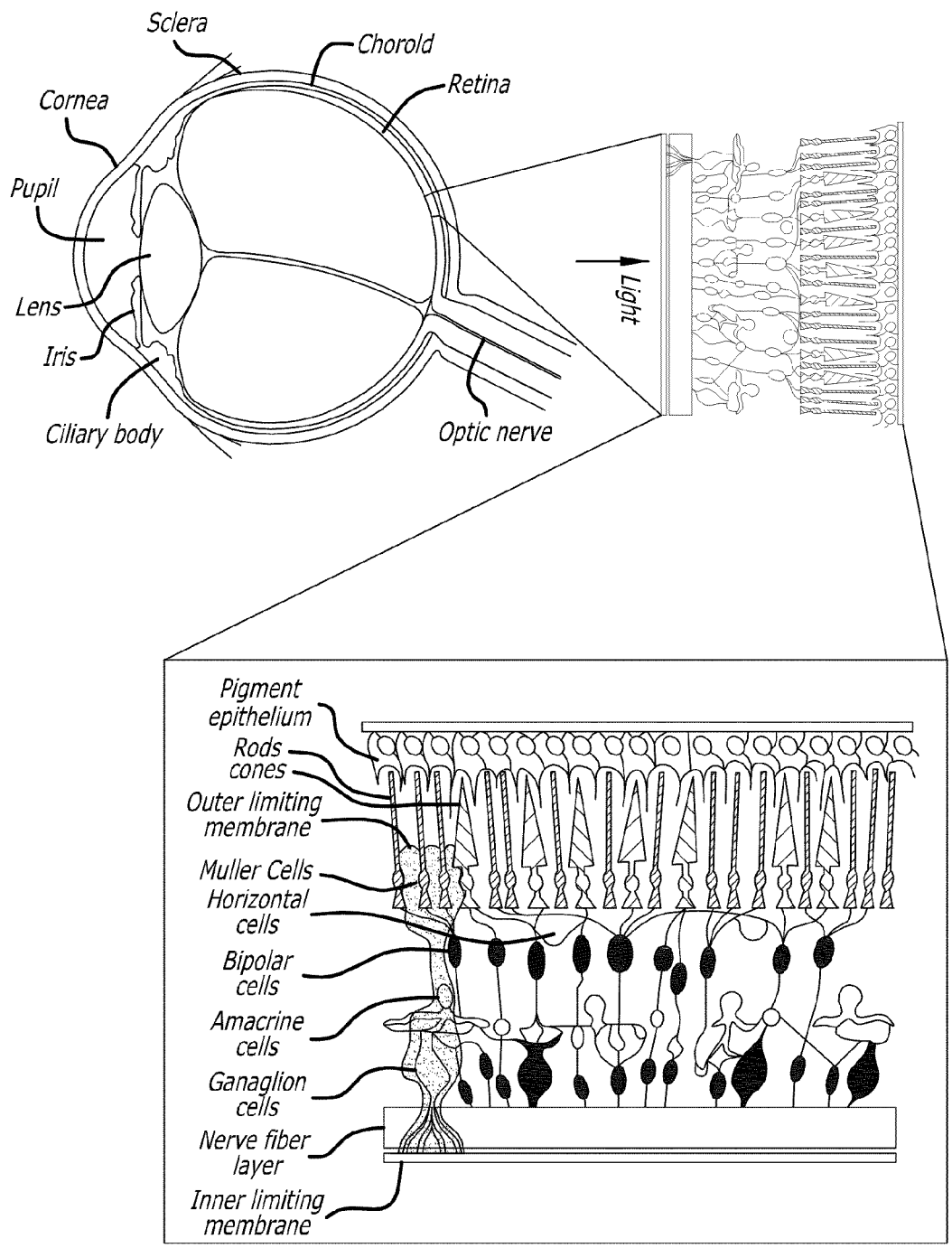
FIG. 2 provides a schematic of the neural anatomy of the eye.

As shown in FIG. 1, the optic nerve function monitoring apparatus/method of the current invention at least comprises a visual evoked potential (VEP) sensor (10). However, to understand the structure and function of this sensor in the current invention it is necessary to understand how the optic nerve functions. In this discussion reference will be made to the schematic of the eye provided in FIG. 2. Specifically, as shown, for a human to see light has to be reflected from an object at an angle so that it strikes the eye and is refracted by the cornea and the lens, and then projects an image on the retina. The optical property of the lens in the eye turns the image upside down and reverses the object (turning it left for right). It is projected onto the retina. The right half of the visual field is projected into the nasal half of the right retina and onto the temporal half of the left retina. The information is then sent on to the left cerebral hemisphere. This schematic is reversed for the left half of the visual field.

The retina itself contains two types of photoreceptor cells. Rods are used for low light vision, such as night vision, and the cones provide high visual acuity and the ability to see colors. Their highest density is found in the vicinity of the fovea centralis, which is located within the macula. The macula is found within the retina and is specialized to provide high visual acuity. The other cells in the eye include receptor cells and bipolar cells, which transmit visual signals to the ganglion cells. The rods and cones connect to the ganglion cells and process information about color and the contrast of images that fall on the retina. Action potentials are generators by these ganglion cells and provide highly processed information about visual images, which are passed onto the thalamus and brain stem.

The axons of the ganglionic cells from the inner surface of the retina come together and then exit the optic disc. Here they become myelinated and form the optic nerve. The optic nerve fibers then pass the optic chiasm, which is found anterior to the Sella turcica, which is directly above the pituitary gland at the base of the brain. The optic fibers partially cross at the chiasm. Fibers from the left and right nasal halves cross. The temporal portions do not cross at the chiasm, but remain on their same original side.

Once the optic fibers pass the chiasm, they become the optic tracks and they continue onto the lateral geniculate body (LGB) where a large number of optic fibers terminate. Each LGB gains input from the retina in a topographic pattern representing the contralateral visual half field. Visual input from the optic tracts and various other projections from the visual cortex and neurons connect with the superior colliculus. The superior colliculus aids in eye movement and then sends visual input in two directions, one to the pons via the tectopontine tract, which relays information to the cerebellum and, two, to the spinal cord via the tectospinal tract. These tracts control head and neck movements in response to visual stimuli.

The pretectal area is found rostral to the superior colliculus. This is an important site for the mediation of pupillary reflexes. Pretectal neurons reach the Edinger-Westphal nucleus in the mesencephalon. Neurons from the LGB form fibers that create the Geniculocalcarine tract, also known as the optic radiations. These fibers reach all of the way to the occipital lobe.

The current invention recognizes that VEPs provide an extremely powerful tool to monitor the function of these complicated neural structures, as they provide a check on the integrity of the visual pathways. In other words, using VEPs it is possible to monitor whether and how the neural structures, such as the optic nerve, chiasm and cortex are carrying electrical signals and any change in those signals. In order to monitor the function of these structures in real-time, the current invention proposes the placement of at least two LEDs, or other equivalent light-emitting device, proximate to the eye. These devices are well known and any of the prior art devices may be used with the current invention. (See, e.g., Celsia, G., et al., American J. of EEG Tech., 25:93-113 (1985 and Erwin, C. W., American J. of EEG Tech., 20:161-184 (1980), the disclosures of which are incorporated herein by reference.) One of the LEDs is provided to stimulate the nasal half of the optic nerve, and the other to stimulate the temporal half of the optic nerve. In addition, a sufficient number of signal receiving electrodes must be placed on the patient to allow for the monitoring of the neural activity generated in response to the LED-generated stimulus. Using such a sensor design it is possible to monitor the function of the two critical structures in the eye—the optic nerve and the optic cortex. In an alternative embodiment, it is also possible to monitor the function of the optic chiasma by the inclusion of an additional LEDs to stimulate the entire surface of the retina periphery to periphery, i.e., from the nasal to the temporal side.

However, while the above provides a bare description of the minimum apparatus required to perform VEP monitoring on a patient, there are a number of different parameters that must be considered in determining the appropriate method of measuring visual evoked potentials to use in accordance with the current invention, including, for example, the type of stimulus, the field of stimulation, the rate of stimulation, what parameters to monitor and record, and the details of how to take a measurement. Each of these parameters will be discussed in detail below. For additional information on standard VEP parameters that can be used in accordance with the current invention see Odom, J. V., et al., Documenta Optha., 108:115-123 (2004), the disclosure of which is incorporated herein by reference.)

Types of Stimulation

Figure 3A:
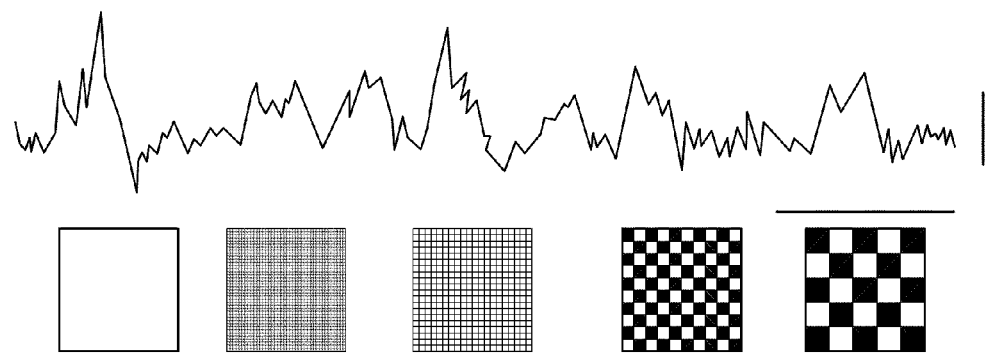
FIGS. 3a and 3b provide exemplary waveforms from visual evoked potentials in accordance with the current invention.
Figure 3B:
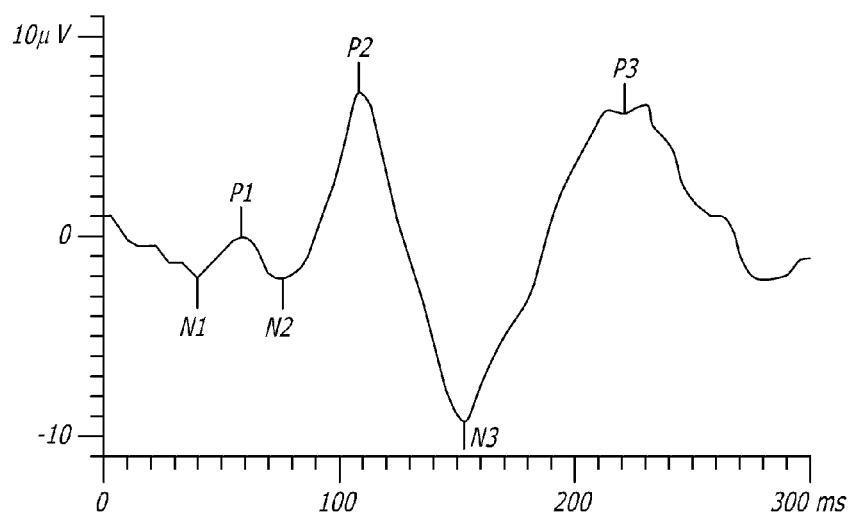

First, to fully monitor the function of optical nerve, the current invention preferably monitors two different types of visual evoked potentials resulting from two different types of stimulus. Schematics of both of these stimuli and associated waveforms are provided in FIGS. 3a and 3b. The first type of stimulus is patterned stimulus (FIG. 3a), such as, for example, alternating checkerboard pattern consisting of sharply defined light and dark squares. Also used are sine wave grating patterns that have dark stripes and a changing brightness between the stripes, such as, bars with well-defined borders or random dots. The visual evoked potential due to a pattern is a result of the density of light and dark contrast in the stimulus. The second type of stimulus is diffuse light (FIG. 3b) used in flash visual evoked potentials. The visual evoked potential waveform from this stimulus comes from the changes in luminescence appreciated by the eye.

For the stimulus, contrast borders should be clear and well defined. A blurring of borders degrades the visual evoked potential pattern. If the check size is too small, the amplitude may be reduced and the latency may increase. The luminance of a patterned light stimulus is measured with a spot photometer. Light and dark elements are measured, the mean is figured, and this is called the mean luminance. Luminance is measured as candela per square meter (cd/ml. The depth of contrast is the difference between the luminance of the light and dark elements divided by their sum, which is expressed as contrast=Lmax−Lmin/Lmax+Lmin. This makes the maximum contrast a value of one and the minimum contrast is a value of zero. For the current invention, a contrast of stimulus set at 0.5 or a 3:1 ratio between minimum and maximum is preferred.

Field of Stimulation

Although these stimuli may be applied to the eye in a number of suitable ways, in one preferred embodiment a hemifield stimulation is provided. To understand what is meant by "hemifield", it is necessary first to understand how a person's "field of vision" is defined. When a stimulus pattern extends beyond both sides of a fixation point (e.g. a dot in the middle of a television screen or checkerboard pattern or a light emitting diode in the middle of a pattern), this is called full field stimulation. A hemifield is one of two halves of a sensory field, i.e., the parts of each visual hemifield that can be seen with both eyes. Although there are a number of ways to accomplish hemifield stimulation, any of which might be used in the current invention, in one preferred embodiment half of the visual stimulation pattern is shown either to the right or left of the visual fixation point, and in another preferred embodiment using the entire stimulus pattern the fixed point is positioned in the left or right margin of the pattern.

Rate of Stimulation

In terms of the rate of stimulation, the typical visual evoked potential in the lab consists of checkerboard pattern reversals at a stimulus rate of two per second. Slower rates of stimulation produce no change in the visual evoked potential where increasing the stimulation rate to four per second may increase the latency of a transient visual evoked potential. Meanwhile, uniform steady state response is usually seen with weights that are six or eight stimuli per second.

Recording Parameters

As discussed above the stimulus in a visual evoked potential may vary; however, in the parameters for recording the various visual evoked potentials are similar for all visual evoked potential types. Specifically, there should be four channels for a complete examination, but fewer channels are required, if only testing the prechiasmal portion of the optic nerve. The American EEG Society Guidelines recommend the following electrode placements, which may be used in conjunction with the current invention:

MO: Midline Occipital, 5 cm above inion;
MF: Midline Frontal, 12 cm above nasion;
RO: Right Occipital, 5 cm right of MO; and
LO: Left Occipital, 5 cm left of MO.

Using these electrodes, the following montage for pattern reversal visual evoked potentials is recommended:

Channel No. 1: RO-MF;
Channel No. 2: MO-MF;
Channel No. 3: LO-MF; and
Channel No. 4: MF-A1.

The actual electrodes should be preferably placed on the scalp in the occipital region in the midline and laterally. Reference electrodes can be preferably placed on the earlobes, frontal, or central scalp.

Measurement Parameters

The low frequency filter should be preferably set at 0.2 to 1.0 hertz and the high frequency filter should preferably be set at 200 to 300 hertz. If the high frequency filter is set at 100 hertz, peak latency may be increased.

For transient visual evoked potentials, the analysis period is 250 milliseconds for normal adults and up to 500 milliseconds for infants or an abnormally delayed visual evoked potential at any age. Before visual evoked potential testing with an awake and alert patient, they should be seated in a comfortable chair in a quiet room. The patient needs to be alert. The patient's visual acuity must be greater than 20/200 or an alteration of visual evoked pattern will occur.

Figure 4:
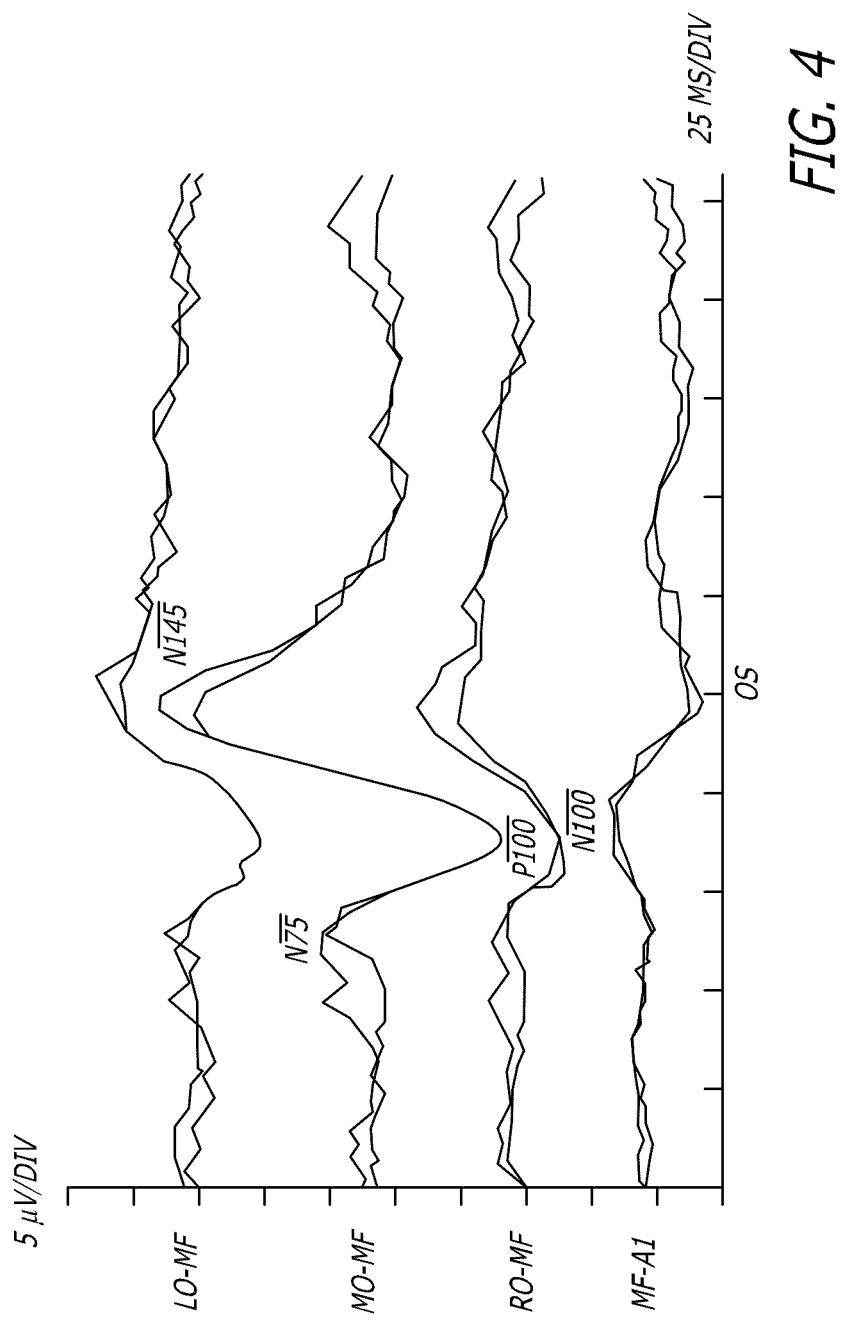
FIG. 4 provides an exemplary waveform from a visual evoked potential in accordance with the current invention.

A typical transient visual evoked potential produced by checkerboard reversal patterns at two per second is reproduced in FIG. 4. As shown the visual evoked potential usually consist of an N-75, P-100, N-145. The waveform starts with a small negative at 60 to 80 milliseconds (N-75) then there is a larger positive occipital peak at a latency of between 90 and 110 milliseconds with amplitude of approximately 10 μV (microvolts). This peak is at P-100. The N-145 is a negative wave following the P-100. The visual evoked potentials should be recorded at least two times and should replicate within 2 to 3 milliseconds to be considered a valid study.

Using the above methodology in accordance with the current invention it is possible to obtain information about the function of the optical nerve of the individual in real-time. In turn, obtain information about the health of the individual. For example, it is well known that many disorders can affect an individual's visual evoked potential. A listing of disorders and possible affects are provided in Table 1, below.

TABLE 1

| Abnormal Full Field Monocular Visual Evoked Potentials | | |
|---|---|---|
| Best Eye | Worst Eye | Abnormality Location |
| Absent VEP | Absent VEP | Bilateral prechiasmal, chiasmal, or retrochiasmal lesion |
| Increased latency | Absent VEP | Chiasmal lesion or bilateral optic nerve lesion |
| Normal | Absent VEP | Optic nerve or ocular lesion |

TABLE 1-continued

Abnormal Full Field Monocular Visual Evoked Potentials

| Best Eye | Worst Eye | Abnormality Location |
|---|---|---|
| Normal | Increased latency | Optic nerve lesion |
| Normal | Normal latency with interocular differences, i.e. the latency in the worst eye is different than the latency in the best eye | Optic nerve lesion |

In addition to the determining abnormalities in the function of the optic nerve, which can, as discussed above, be identified and diagnosed using visual evoked potentials, visual evoked potentials can also be used to identify and diagnose a wide-variety of broader disorders, as shown in Table 2, below.

TABLE 2

How Do Disorders Affect Visual Evoked Potential

| Disorder | Affect |
|---|---|
| Alcoholism | Increased latency is possible |
| Charcot-Marie-Tooth | Delayed visual evoked potential |
| Muscular dystrophy | Delayed visual evoked potential |
| Chronic renal failure | Reduced amplitude and possible increase in latency |
| Cataracts | Reduced amplitude and possible increase in latency |
| Corneal opacities | Reduced amplitude and possible increase in latency |
| Diabetes | Delayed visual evoked potential |
| Downs Syndrome | Low amplitude with delayed visual evoked potential |
| Endocrine orbitopathy | Delayed visual evoked potential |
| Glaucoma | Increase latency of visual evoked potential |
| Hysterical blindness | Normal visual evoked potentials |
| Optic nerve trauma | Decrease amplitude and optic nerve tumors increased latency and decreased amplitude or may have been completely absent |
| Retrobulbar neuritis | The affected side may have increased latency and decreased amplitude |

Celesia G, et al., American Journal of EEG Technology, 25: 93-113 (1985), the disclosure of which is incorporated herein by reference.

Figure 5:
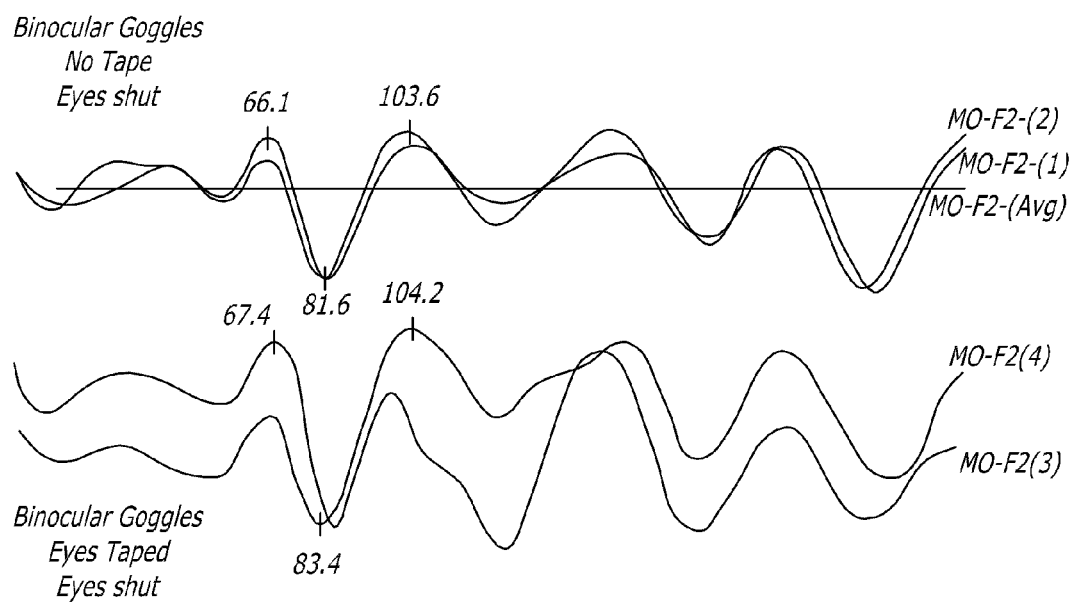
FIG. 5 provides an exemplary waveform from a binocular visual evoked potential in accordance with the current invention.

During operation, as shown in FIG. 1, a visual evoked potential sensor, such as a light emitting diode device is applied over the eye. The eye may be optionally "taped shut" to ensure that the sensor is not dislodged by the patient. Regardless, as shown in FIG. 5, below, the intensity of the stimulus is enough to pass through the eyelid and tape. Specifically, the upper tracing is binocular with goggles, no tape, and the eye is shut. The lower tracing is with Transpore® tape taping the eye shut. The waveform amplitude and latencies are comparable, although there appears to be a variation in the latency between the dominant and the non-dominant eye of approximately 1.0 to 1.25 milliseconds. Although any type of visual evoked potential sensor may be used, the use of LED goggles, which are placed directly over the eyes, have the advantage of producing a very large field of stimulation and minimizes the affect of changes in direction of gaze. The stimulation usually takes place through closed eyelids. Although a number of different goggle designs can be used, in a preferred embodiment the LED is be placed in the middle of the goggle because having the LED placed laterally or medially would stimulate one of only the nasal field or temporal field not both.

Although the above parameters and procedures may be generally used, it should be understood that some modifications must be made based on the demographic of the patient. For example, Shaw, et al., showed that at lower levels of luminance there was a significant difference between those under 40 and those over 40 in the latency of P-100. This was very clear in those in their fifties. At higher levels of luminance, there was no significant increase in the latency at P-100. (Shaw N. A., et al., Electroencephalography and Clinical Neurophysiology, 48:237-241 (1980), the disclosure of which is incorporated herein by reference.) There are a number of changes in visual function associated with aging, which underlies the increase in the latency of P-100. There was a decrease in pupillary diameter, increase in opacity of the lens, which results in an essentially linear decrease in the amount of light reaching the retina between the ages of 20 and 60 years. (Corso J F, Journal of Gerontology, 26:90-105 (1971), the disclosure of which is incorporated herein by reference.) Similarly, neuroaxonal dystrophy is described in the central nervous system beginning at the age of 20 as becoming more severe by the age of 50. (Sung J. H., Journal of Neuropathology and Experimental Neurology, 23:567-583 (1964), the disclosure of which is incorporated herein by reference.) There is also a demonstrable loss of neurons in the striate cortex in the fifth decade. (Brody, H., Journal of Comprehensive Neurology, 102:511-566 (1955), the disclosure of which is incorporated herein by reference.)

In addition, there are more subtle changes, such as the loss of dendrites and changes in neurotransmitter function. (Samorajski T., of American Geriatric Society, 25:337-348 (1977) and Scheibel M. E., et al., "Structural Changes in the Aging Brain: Volume I, Clinical Morphologic and Neurochemical Aspects in the Aging Central Nervous System", Ravencrest, N.Y., 1975:11-37, the disclosures of which are incorporated herein by reference.) There is increased synaptic delay, which contribute to increased latency associated with increasing age. (Wayner M J, Emers R, American Journal of Physiology, 194:403-405 (1958), the disclosure of which is incorporated herein by reference.) In short, it is important when looking at visual evoked potentials to consider neurological diagnoses, consider the age of the subject, and consider the level of luminance used. (For a more detailed discussion see the references above and Allison T., et al., Electroencephalography and Clinical Neurophysiology, 58:14-24 (1984); Erwin C. W., American Journal of EEG Technology, 20:161-184 (1980); Gilman S., et al., "Essential of Clinical Neuroanatomy and Neurophysiology", 1996, FA Davis Company, Philadelphia; Skrandies W., Neuro. Report, 10:249-253 (1999); and Weale R. A., Trans. Opthal. Soc. UK, 95:36-38 (1975), the disclosures of which are incorporated herein by reference.)

Intraocular Pressure Sensor

As shown in FIG. 1, another optional sensor that may be used with the method/apparatus of the current invention is an intraocular pressure (IOP) sensor (12). The intraocular pressure sensor, like the VEP sensor is place against the closed and/or taped eyelid of the patient and connected an external monitor. Any pressure transducer sensor suitable for monitoring intraocular pressure may be used, such as, for example, a tonometer. (See, e.g., Amm M., et al., Opthalmologe. 102 (1):70-6 (2005), the disclosure of which is incorporated herein by reference.)

As discussed above, in one embodiment of the invention the IOP is measured via a tonometer. There are a number of different types of tonometeric techniques that may be used with the current invention, such as, for example, apponation tonometry, Goldmann tonometry, dynamic contour tonometry, diaton tonometery, non-contact tonometry, impression, tonometry, rebound tonometry, Schiötz tonometry, and Perkins tonometer. However, in one preferred embodiment, the invention uses transpalpebral tonometery, which measures intraocular pressure through the eyelid by a diaton tonometer. Transpalpebral tonometry requires no contact with the cornea, therefore sterilization of the device and topical anesthetic drops are not required and there is very little risk of infection. (See, e.g. Davidson, R. S., et al., ASCRS/ASOA, Poster #P-130 (2007); Theodore H. Curtis, et al., ASCRS/ASOA, Poster #P-128 (2007); Lam A. K., et al., Ophthalmic Physiol Opt. 25(3):205-10. (2005); Henry D. Perry, Eyeworld Magazine (2006); Nesterov A. P., et al., Vestn Oftalmol. 119(1):3-5 (2003); Sandner D., et al., Graefes Arch Clin Exp Opthalmol. 243(6):563-9 (2005); and Troost A, et al., Br J Opthalmol. 89(3):280-3 (2005), the disclosures of which are incorporated herein by reference.)

Although it is not essential to the operation of the optic nerve function apparatus/method of the current invention, it is preferred that the intraocular pressure be monitored as well, because an increase in intraocular pressure can signal potentially serious disorders. (See, e.g., U.S. Pat. No. 7,314,454, the disclosure of which is incorporated herein by reference.) For example, rising intraocular pressure is known to decrease ocular perfusion pressure even where normal mean arterial pressure is maintained. In turn, reduced ocular perfusion (or a decrease in oxygenated blood) being supplied to the optic nerve can stress the nerve ultimately resulting in substantial damage, such as, for example, posterior ischemic optic neuropathy.

Moreover, significant changes in intraocular pressure are a common side effect of anesthesia, particularly where patients are placed into prone positions for long periods of time. For example, in a study of awake volunteers, intraocular pressure increased in an article by Cheng in 2001 from 13.5 millimeters of mercury, plus or minus 2.01 in the sitting position, to 20 millimeters of mercury, plus or minus 3.27 in the prone position. Cheng, M. D., et al., Anesthesiology, 95:6, 1351-1355 (2001), the disclosure of which is incorporated herein by reference.) Other studies have shown that sequentially over time, intraocular pressure increases. It increases by 100% after four hours. This may be due to a number of issues. For example, the prone position increases intraperitoneal pressure, central venous pressure, peak inspiratory pressure, and intraocular pressure. Intraocular pressure has been shown to increase in anesthetized patients who are supine in a head down Trendelenburg position and in our study of awake inverted volunteers, there was a considerable increase in intraocular pressure over time. The mechanism for that increase may be related to higher episcleral venous pressure. Freiberg, et al. in 1985 found 1 millimeter of mercury increase in intraocular pressure for every 0.83 millimeters of mercury episcleral venous pressure. A slightly head neutral or head up position may attenuate the observed increase of intraocular pressure in the prone position. However, beyond the position of the patient increased arterial carbon dioxide tension can produce an increase in intraocular pressure, demonstrated by Hvidberg in 1981. Increased intraocular pressure may also be related to observed positive intraoperative fluid balance. In an experiment carried out by Brucculeri in 1999, healthy volunteers were given acute oral water loading, 14 ml per kilogram, and the intraocular pressure increased. Martin, in 1999, demonstrated that exercise-induced dehydration reduced intraocular pressure. Decreased serum osmolality during dialysis increased intraocular pressure in patients with renal failure. (See, Tawara (2000), the disclosure of which is incorporated herein by reference.) In another study performed by Evans in 1991, severely burned patients were found to have very elevated intraocular pressures in the range of 37.2 to 81.7 millimeters of mercury due to extreme orbital congestion related to large amounts of intravenous fluid.

Indeed, even elevations of central venous pressure (CVP) have been shown to contribute to increased intraocular pressure. (See, e.g., Kamming D., et al., British Journal of Anesthesia, 95:257-260 (2005), the disclosure of which is incorporated herein by reference.) Although not to be bound by theory it is believed that it is increased by reduced venous return in patients in the head down position and obstruction of venous outflow, such as the ligation of veins in radical neck surgery. Blood flow in the posterior optic nerve is susceptible to increased venous pressure because the arterial supply to the posterior optic nerve is derived from small end vessels from the surrounding pia. Indeed, there are case reports of ischemic optic neuropathy that occurred in patients associated with increased venous and intracranial pressure after radical neck operations with bilateral jugular vein ligation. Turning the head to one side or the other can restrict venous outflow. Central venous pressure can be increased if there is direct pressure on the abdomen due to poor positioning on the operating table during prone anesthetic. In a patient who is correctly positioned and who has central venous pressure between six to thirteen millimeters of mercury, this might not be seen as a single significant factor in optical nerve trauma, such as, for example, visual loss. However, CVP readings may not necessarily reflect venous pressure inside the globe and there may be marked venous congestion of the head and neck, even with a normal CVP reading.

In short, it is important to remember that increased intraocular pressure and concomitant reduced ocular blood flow that results may be caused by a number of factors, which individually may not seem significant, but cumulatively increase the risks to a patient. Moreover, simply monitoring venous pressure often gives inaccurate information on the physiology of the optic nerve because an increase in intraocular pressure can lower ocular perfusion pressure despite the maintenance of a normal mean arterial pressure. Accordingly, an intraocular pressure sensor, such as that described in the current invention, provides a more accurate measurement of the stress on and function of the optic nerve than do other types of monitoring.

Ocular Blood Flow Sensor

Finally, another optional sensor that can be used in combination with the VEP and intraocular pressure sensors is a blood flow sensor (14), which as with the VEP and IOP sensors is attached or positioned near the surface of the closed and/or taped eyelid of the patient. As discussed above in relation to the IOP, one of the most serious stresses that can be placed on the optic nerve during anesthesia is a reduction or loss in blood flow to the optic nerve. Although the VEP and IOP sensors can provide information on blood flow to the eye indirectly by measuring other parameters such a neural function and IOP that are impacted by a change in blood flow or perfusion, having a direct measurement of blood flow to the eye and optic nerve would provide a more certain measurement of this critical parameter.

Specifically, in one embodiment of the invention a blood flow sensor is provided that can measure the function of the choroidal arteries supplying the eye with blood, and in a most preferred embodiment, that can measure the flow of blood to the optic nerve itself. Even though choroidal blood flow is not directly analogous to central retinal artery blood flow, it does provide a baseline evaluation of perfusion of the optic disk and the optic nerve head. As such, beyond providing a simple measure of the function and general health of the eye, it can also be used in preventing the possibility of iatrogenically induced ischemic optic neuropathy.

Although any number of indirect methods can be used to measure blood flow, in a preferred embodiment either laser Doppler velocimetry or near-infrared spectroscopy can be used to make instantaneous measurements of the flow of blood to and into the eye. Laser Doppler Velocimetry (LDV) is a technique that fluid mechanics and researchers use to make instantaneous velocity measurements (magnitude and direction of fluid flow). (For a full description see, Durst F., et al., "Principles and Practice of Laser Doppler Anemometry", Academic Publishers, New York, 1976 and Adrian R. J., Editor, Selected Papers on Laser Doppler Velocimetry, Spine Milestone Series, MS 7,8, Spie Optical Engineering Press, Bellingham, Wash., 1993, the disclosures of which are incorporated herein by reference.) LDV utilizes the concept of the coherent wave nature of laser light. The crossing of two laser beams of the same wavelength produces a pattern. It produces areas of constructive and destructive interference patterns. The interference pattern is known as a fringe pattern and is composed of planar layers of high and low intensity light. Velocity measurements are made when particles seated in the flow pass through the fringe pattern created by the intersection of a pair of laser beams. The particles scatter light in all directions. The scattered light is then collected by a stationary detector. The frequency of scattered light is Doppler shifted and referred to as a Doppler frequency of the flow. The technique is nonintrusive and can deliver measurements independent of ambient conditions. It measures three directional components and it can access any flow region with the aid of fiberoptics. It has a range (dynamic range) from natural convection to supersonic velocities.

In one such embodiment, the laser power source for the LDV in accordance with the current invention is a helium/neon (HeNe) or argon ion laser with a power of ten milliwatts. Lasers have advantages over other radiation wave sources, including excellent frequency stability, small beam diameter, and high focused energy. Laser Doppler can be configured to act as flow meters or anemometers by evaluating the velocity of reflected particles entrained in a transparent flow field. In the current invention, the LDV can be attached directly to the eye, or mounted in a set of goggles that protect and support the eye, thereby allowing real-time measurement of choroidal blood flow.

In another embodiment, near-infrared spectroscopy could be used to monitor blood flow to the eye. Optical photons are insufficiently ionized and unless light is concentrated to such a high degree that it causes burning to the skin, optical radiation is not a significant hazard. Accordingly, the diagnostic potential of optical methods has been known since Jobsis, in 1977, who first developed transmittance measurements of near infrared radiation and showed it could be used to monitor the degree of oxygen related metabolites. (Jobsis F. F., Science, 198:1264-1268 (1977), the disclosure of which is incorporate herein by reference.) This led to the development and increasingly widespread use of clinical near infrared spectroscopy, which offers a safe, noninvasive means of monitoring cerebral function at the bedside without the use of radioisotopes. (Coke M., et al., "Medicine and Biological Engineering and Computing", 26:289-294 (1988), the disclosure of which is incorporated herein by reference.) Indeed, even tissues contain a variety of substances whose absorption spectra at near infrared spectroscopy wavelengths are well defined, including oxygenated hemoglobin ($HbO_2$), deoxyhemoglobin (Hb), and tissues which are strongly linked to tissue oxygenation and metabolism increasing the dominant absorption wavelengths limits spectroscopic studies to less than approximately 1,000 meters.

Accordingly, using this technique it is possible to quantify changes in tissue oxygenation can be evaluated in a noninvasive way and quantifies changes in the concentration of deoxyhemoglobin and oxygenated hemoglobin in units that are micromolar can be used to study hemodynamic parameters, such as cerebral blood flow, and, therefore, evaluate flow of the blood vessels in the eye (choroidal blood flow). (Edwards A. D., et al., Lancet, 770 (1988) and Wyatt J. S., et al., "EOR", 1086-1091 (1990), the disclosures of which are incorporated herein by reference.) As such, a near-infrared spectrometer could be incorporated into a sensor band or goggles positioned proximate to the eye to provide a method to evaluate blood flow in the choroidal system and the optic nerve head.

Location Sensor

In addition to monitoring physiological information about the eye and optic nerve, as shown in FIG. 1, in another optional embodiment a sensor may be included to measure the location and movement of the eye (15). To understand the potential importance of this sensor it is necessary to understand the stresses placed on the eye during a typical surgery. When a patient is anesthetized the patient's eye are taped or sewn shut and a protective device placed over them because otherwise the eyes could open and dry resulting in trauma. Also, during the surgery the patient is often placed into downward angled or downward facing positions. The result is that the eyes of the patient are susceptible to two types of trauma. First, because of the presence of the tape and protective device external pressures can inadvertently be applied to eye if the patient's head rolls or moves relative to these devices. In addition, if the patient is placed facing downward the force of gravity can pull the eye downward out of the eye socket fractionally. Although these direct or indirect forces might be relatively small, the delicacy of the nerve and the weakness of the vessels that supply blood to the optical structures, can lead to a drop in circulation to the eye, which in turn can lead to damage to the optic nerve or other structures.

The current invention recognizes that monitoring the position and movement of the eye during surgery using a simple pressure transducer can supply the treating physician with important information about the force being placed on the eye, and allow the physician to mitigate those forces, such as by repositioning the patient, should they reach a dangerous threshold level.

Any suitable pressure sensor capable of converting the movement of the eye to an electrical signal that can be monitored by an external device may be used in accordance with the current invention. In one preferred embodiment, the pressure sensor is a solid state MEMS pressure transducer that can be applied directly to the closed eyelid of the patient. An example of a suitable pressure sensor is described in U.S. Pat. No. 7,314,454, the disclosure of which is incorporated herein by reference.

Figure 6:
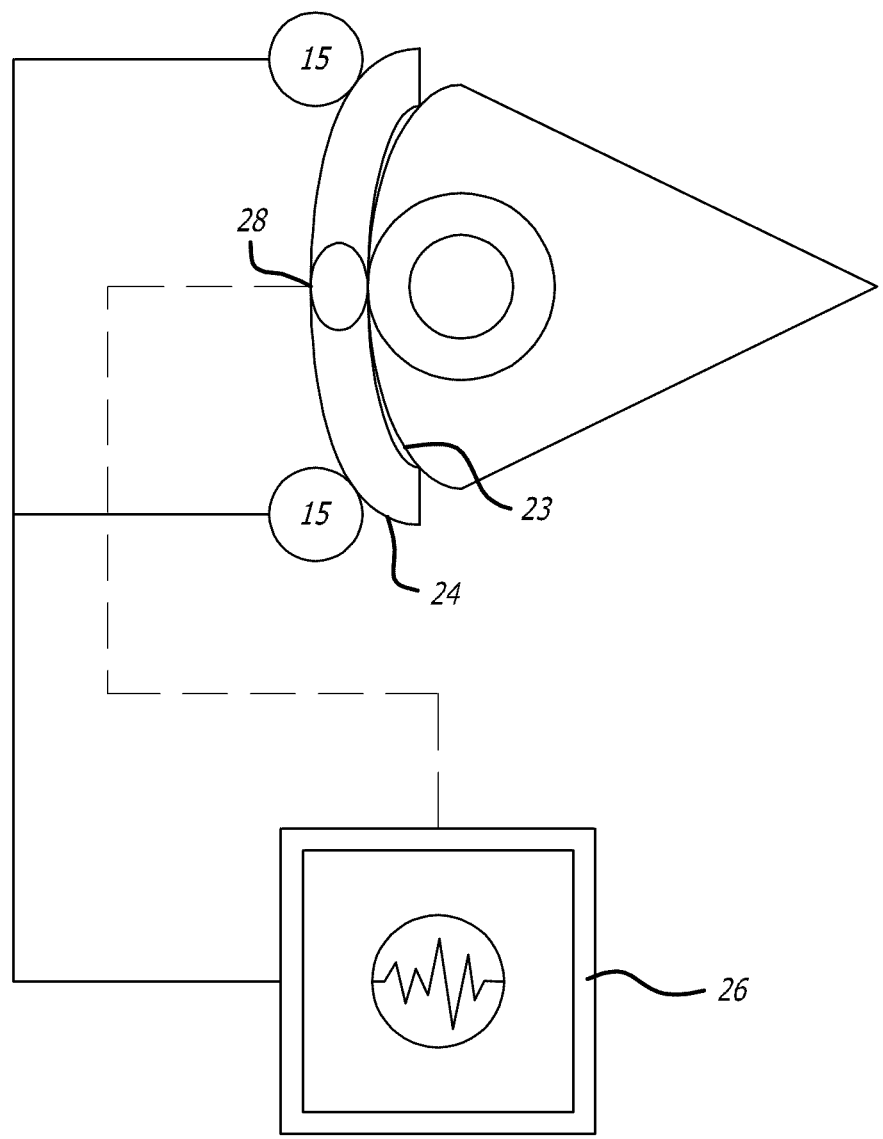
FIG. 6 provides a schematic diagram of an active eye support apparatus in accordance with one exemplary embodiment of the current invention.

Although the above description has focused on an embodiment comprising a passive eye position and movement sensor, it should be understood that such a sensor can optionally be combined with an active feedback system to neutralize the forces being felt by the eye by actively fixing the position of the eye in its correct anatomic location relative to the socket. Such an embodiment, shown schematically in FIG. 6, incorporates a support mechanism (24) that would be placed into contact with the outer surface of the eyelid (16) to fix the eye into the correct anatomical placement and apply appropriate pressure on the eye to ensure this placement is maintained based on the signals supplied by the location sensor (15). In accordance with the current invention any suitable support mechanism and actuator capable of providing a force sufficient to adjust the position of the eye, such as, for example, an air bladder, hydraulic sleeve or electromechanical actuator. In addition, the structure of the support mechanism itself may take any form suitable for placement against the eyelid, including, for example, a bladder, pad or contoured cup.

During operation the signal from the location/movement sensor (15) is sent to a signal processor/controller (26) that then activates the support mechanism (24) to neutralize the movement of the eye to keep the eye in its proper anatomical placement within the eye socket. In an alternative embodiment the active support mechanism (24) is further supplied with a pressure sensor (28), such as, for example, an electronic pressure transducer that would monitor the pressure being applied to the eye by the active support mechanism (24). In such an embodiment, safety thresholds and limits can be preprogrammed into the controller (26) such that the pressure being applied never exceeds a level that can be safely tolerated by the eye.

Sensor Apparatus

Figure 7:
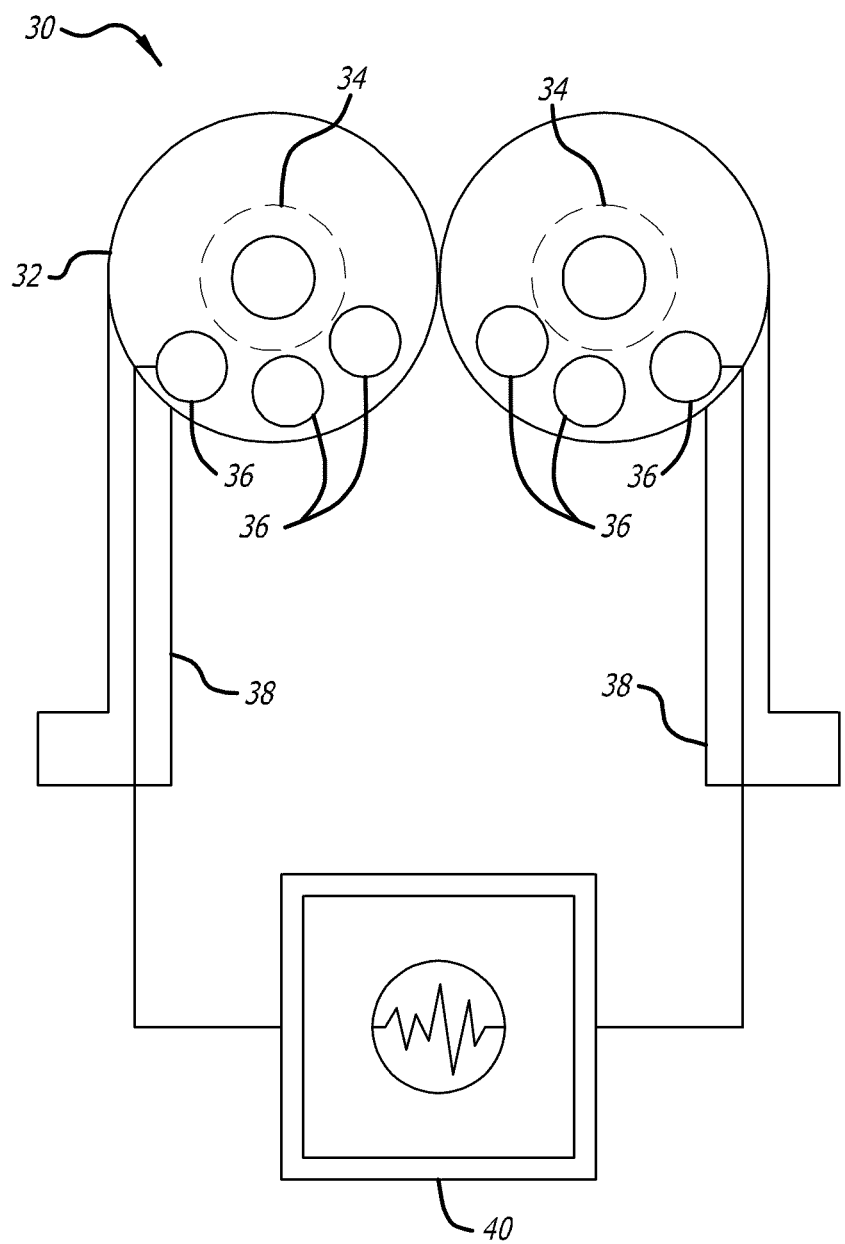
FIG. 7 provides a schematic diagram of an exemplary optic nerve function goggle apparatus in accordance with the current invention.

Although the above discussion has focused on the construct and operation of the individual sensors, it should be understood that the current invention is also directed to an apparatus for positioning and holding the sensor into position on a patient during use. Although any construct capable of placing and holding the sensor(s) in place proximate the patient's closed eye during use may be used, in a preferred embodiment the sensors are integrated into a pair of goggles (30) as shown in FIG. 7.

Although the goggles (30) can take a number of different forms, there are a few necessary elements. First, as shown in FIG. 7 the goggles should have a main body (32) capable of covering both eyes (34) sufficient to incorporate the package of sensors (36) in a position proximate to the eyes of the patient. The goggles also incorporate leads (38) or other means wired or wireless to transmit the signals from the sensors (36) to an external monitor (40) that can communicate the signals to a physician.

The goggles may be made of any suitable material. Preferably the goggles are of a disposable one-use construction made from surgical grade materials to ensure that the possibility of cross-contamination between patients is avoided.

The above general statement of the invention will be better understood with reference to the embodiments of the invention provided in the examples detailed in the following sections. It should be understood that these examples are only provided for further detail of preferred embodiments of the invention, and the scope of the invention is not to be considered to be constrained by or to the those embodiments.

EXEMPLARY EMBODIMENTS

As discussed above, monitoring a patient's optic function when in a state of altered consciousness can provide important information to a physician about both the mental and physical state of the individual at a time when the patient himself is unable to communicate. However, beyond this general benefit to optic monitoring, it is also possible to provide the physician information that can help them diagnose, and potentially prevent, the occurrence of anesthesia-induced disorders that are currently difficult if not impossible to detect until after the patient has regained consciousness.

Two examples of disorders that can be diagnosed using the optic function monitor of the current invention are described in the sections below.

Example 1

Post-Operative Visual Loss (POVL)

Post Operative Visual Loss (POVL) is a broad term that is often discussed as a single condition; however, there are actually a number of conditions that fall within this broad definition, including, for example, posterior ischemic optic neuropathy (PION), anterior ischemic optic neuropathy (AION), and central retinal artery occlusion (CRAO). Currently there is a great deal of dispute as to what factors play a role in causing POVL. As a result, there is no known methodology for monitoring and preventing POVL in real-time. Before providing a description of how the apparatus/method of the current invention may be used to monitor, diagnose and potentially prevent POVL, it is important to understand the spectrum of disorders that fall within this broad classification.

Corneal Abrasion and Scleral Injury

Corneal abrasion is the most common surgical and general anesthesia-related eye complication. (See, e.g., Batra Y. K., et al., Anesthesia and Analgesia, 56:363-365 (1977); Slocum H. C., et al., Surgery Gynecology and Obstetrics, 86:729-732 (1948) ; and White E. & Cross E., Anesthesia, 53:157-163 (1988), the disclosures of which are incorporated herein by reference.) The injury is usually the direct result of lagopthalmos (the incomplete closure of the eye). General anesthesia reduces tear formation and stability. If the eyelid does not cover the cornea, the cornea may become dry, thus increasing the likelihood of irritation, abrasion, or laceration. Uveal inflammation and secondary infection increased after abrasions. The standard method of preventing corneal abrasions is secure taping of the eye. One alternative that has actually appeared in the literature is to have the eyelids sewn shut prior to prone positioning of the patient. (See, Cucchiara R. F. & Black S., Anesthesiology, 69:978-979 (1988), the disclosure of which is incorporated herein by reference.)

When corneal abrasions are identified postoperatively, an opthalmological consultation is recommended and the usual treatment is topical eye antibiotic. (See, Daughtery R. J., Clinical Pediatrics, 2002; 41:630, the disclosure of which is incorporated herein by reference.) Topical anesthetics are to be avoided, as they will delay corneal epithelialization and promote keratitis. If anesthetic drops are used, an extension of the abrasion may occur if the patient was to rub or scratch the anesthetized eye. Although corneal abrasions can be relatively benign, there are occasions where a corneal ulcer derived from an abrasion can cause partial or complete visual loss on the involved eye.

Central Retinal Artery Occlusion

Central retinal artery occlusion (CRAO) is the second most common cause of postoperative blindness associated with prone positioning and general anesthesia. (Stambough J. R., et al., Journal of Spinal Disorders, 5:363-365 (1992), the disclosure of which is incorporated herein by reference.) Central retinal artery occlusion is described as a stroke of the central retinal artery. Central retinal artery occlusion after surgery is usually caused by direct or indirect pressure on the eye, which increases intraocular pressure, basilar spasm, or displacement of plaques from the carotid artery may enter the central retinal artery (Hollenhorst plaques). (Hollenhorst R. W., et al., Archives of Opthalmology, 52:819-839 (1954), the disclosure of which is incorporated herein by reference.) Perioperatively, central retinal artery occlusion occurs associated with direct pressure from prone positioning. The hallmark of this diagnosis is the cherry red spot on the center of the macula. This is seen on funduscopic examination. CROA is commonly reported secondary to prominent headrest and direct orbital pressure, which increases intraocular pressure and decreases retinal blood flow through the central retinal artery producing the headrest syndrome coined by Katz DA in 2005. (Katz D. A., et al., Spine, 30:E83-E85 (2005), the disclosure of which is incorporated herein by reference.)

There are anatomic variations, which predispose towards the occurrence of central retinal artery occlusion, including a small nasal bridge, exophthalmus, a small cup to disc ratio, a narrow cribrosus lamina, or microvascular anomalies in the eye. It is also associated with osteogenesis imperfecta. An examination showed evidence of external periorbital swelling or ecchymosis. Central retinal artery occlusion is not painful, but there is secondary irritation from the direct source, i.e. the sclera and associated structures may be edematous, which is an obvious indication of external compression. Intraocular pressure exceeds the perfusion pressure of the central retinal artery producing ischemia of the retina. Most patients will have unilateral loss of vision often resulting in permanent amaurosis.

Blindness from central retinal artery occlusion is always irreversible. However, Takeuchi, et al. reported a case of partial visual loss associated with central retinal artery occlusion that was treated aggressively with Dexamethasone, Paverine, and Pentoxifylline. (West J., et al., British Journal of Opthalmology, 74:243-244 (1990), the disclosure of which is incorporated herein by reference.) After spine surgery, central retinal vein occlusion has been reported in associated CRAO. It is always secondary to increased intraocular pressure and a low flow state from primary pathophysiology leading to CRAO. (Bradish C. F., et al., Spine, 12:193-194 (1987), the disclosure of which is incorporated herein by reference.) To date, there are no consistently effective treatments for central retinal artery occlusion.

Cortical Blindness

Cortical blindness is caused by an isolated cerebrovascular accident that selectively affects the visual cortex in the occipital lobes. It is usually associated with an embolus or hypoperfusion of the visual cortex of the central nervous system, such as that shown in the MRI provided in FIG. 8. (See, Drymalski W. G., Postgraduate Medicine, 67:149-156 (1980), the disclosure of which is incorporated herein by reference.) Many causes have been associated with this condition including cardiac arrest, profound hypotension, and air embolus. Another reported cause is difficult intubation with prolonged hypoxia and cyanosis. The hallmark finding in cortical blindness is the normal funduscopic examination and the retention of pupillary reaction to light with the associated decreased vision. Cortical blindness is usually bilateral. Clinical features include failure to react to threatening gestures, no response to optokinetic stimulation, and consistent electroencephalogram changes to photic stimulation. Patients present with Anton's Syndrome, an unusual condition in which a patient who lost vision because of visual cortex ischemia or infarct will deny blindness. This is also called anosognosia and might be confused with hysterical conversion reaction.

Figure 8:
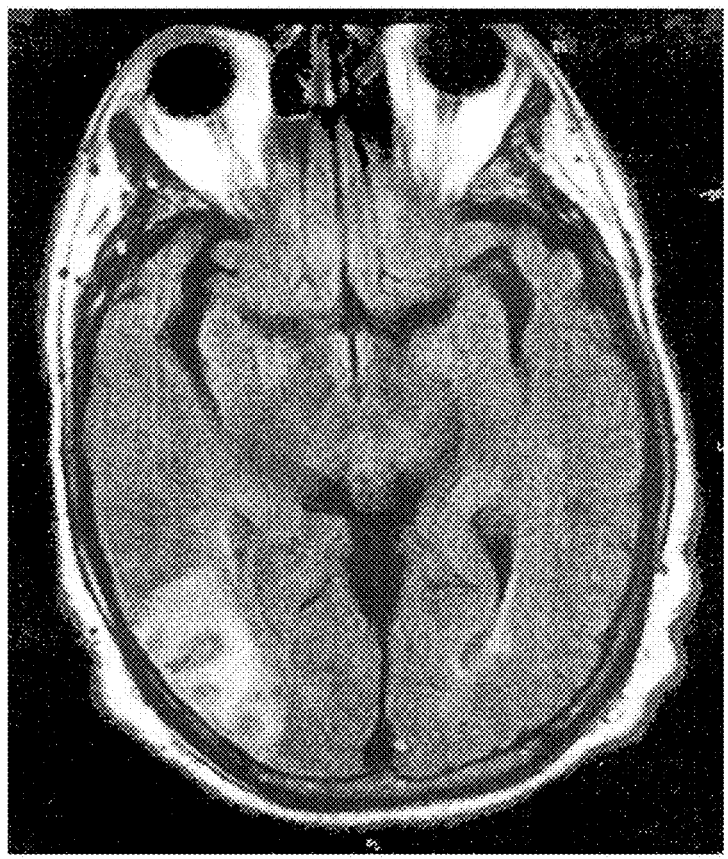
FIG. 8 provides an MRI of showing an embolus or hypoperfusion of the visual cortex associated with cortical blindness.

The MRI picture shown in FIG. 8 demonstrates an infarct in the left occipital lobe of a patient who had temporary cortical blindness. The blindness manifested as a decreased ability to concentrate, lethargy, and nonspecific visual impairment after an elective right total knee arthroplasty. During the case, hypotension or hemodynamic changes were not observed related to anesthesia. Blindness subsequently was thought to be embolic as the patient had a documented atrial septal defect. The visual impairment was noted the day after surgery. Opthalmologic examination showed hemianopsia in the outer quadrant of the right eye and the inner quadrant of the left eye. Neurologic and vascular evaluations found no plaque in the carotid artery or source of embolism.

Other abnormalities can also produce cortical blindness, such as an air embolism in the sitting position during cervical spinal osteotomy. (Stevens W. R., et al., Spine, 1997; 22:1319-1324, the disclosure of which is incorporated herein by reference.) Air embolism during central venous catheterization in combination with a rapid turning over of the patient or in pediatric patients with septal defects may cause unilateral or bilateral homonymous hemianopsia (the loss of half of the visual field on the same side in both eyes). (See, Hoski J. J., et al., JBJS America, 75:1231-1232 (1993) ; Jaben S. L., et al., Clinical Neuroopthalmology, 239-244 (1983) ; Wolfe S. W., et al., Spine, 17:600-605 (1992) ; and Yanagidate F., et al., Journal of Anesthesia, 17:211-212 (2003), the disclosures of which are incorporated herein by reference.) Homonymous hemianopsia acts like a transient ischemic attack. Additionally, transient hemianopsia may be considered a partial manifestation of cortical blindness. Homonymous hemianopsia has been reported in patients who have cardiac defects, such as atrial septal defects. Perioperative echocardiograms with three-dimensional imaging can heighten the diagnosis of atrial septal defects and the potential of embolic phenomena. (See, Takahashi S., et al., Journal of Bone and Joint Surgery, British, 85:90-94 (2003), the disclosure of which is incorporated herein by reference.)

Ischemic Optic Neuropathy

Ischemic optic neuropathy (ION) results from infarction of the intraorbital optic nerve. The infarction occurs as a result of decreased oxygen delivery due to perioperative hemodynamic derangements. There appear to be many subtle factors which, when acting in concert, produce decrease in the amount of oxygenated blood that comes to the optic nerve resulting in posterior ischemic optic neuropathy.

Various risk factors and causes of factors have been considered, including hypotension, increased venous pressure, head-down operative position, increased cerebrospinal fluid pressure, direct ocular compression (more important in central retinal artery occlusion), and embolism. Also, the breakdown of the autoregulation of the perfusion of the optic nerve and eyes that have a greater risk due to poor autoregulation would be seen in patients who have comorbidities, such as diabetes, elevation of blood pressure, vasculitis, over the age of fifty, etc. Indeed, in most of the instances of perioperative posterior ischemic optic neuropathy, more than one hemodynamic parameter was altered, suggesting that the mechanism causing infarction is produced by the combination of factors, not one sole factor.

There would appear to be at least three basic ways hemodynamic derangement leads to decreased oxygen delivery to the optic nerve. There can be a decrease in arterial perfusion pressure and an increase in resistance to blood flow or a decrease in blood oxygen carrying capacity. When the cases evaluated by the American Society of Anesthesiologists Postoperative Visual Loss Registry, some of these factors were always present in patients who developed posterior ischemic optic neuropathy. Combinations of anemia and hypotension are seen in the majority of the cases. Perioperative anemia and hypotension can lead to decreased blood oxygen carrying capacity and decreased arterial perfusion pressure. Anemia can result from uncorrected preoperative chronic anemia or due to intraoperative blood loss and/or hemodilution. Hypotension can result from hypovolemia or can be deliberately induced in some cases to diminish blood loss during spinal surgery.

Even though perioperative anemia and hypotension existed in many of these cases, those two factors are common in the perioperative course of many surgical procedures, especially spine surgery, cardiopulmonary bypass, etc. Only a small number of patients actually develop posterior ischemic optic neuropathy. This fact alone argues against hemodynamic factors as being the exclusive reason for this problem to occur. Moreover, Myers, in 1997, actually compared patients who had sustained postoperative visual loss after spine surgery to an unaffected control group and showed quite clearly that perioperative hematocrit and blood pressure were no different in the two groups. (Myers M. A., et al., Spine, 22:1325-1329 (1997), the disclosure of which is incorporated herein by reference.)

Increased orbital venous pressure can lead to a decrease in arterial perfusion pressure and may be involved in the pathogenesis of this condition. Internal jugular vein ligation often part of a radical neck dissection can cause rapid and severe increase in venous pressure in the head and orbit, which results in massive facial and orbital edema. (Balm A. J., Journal of Laryngol Otol, 104:154-156 (1990), the disclosure of which is incorporated herein by reference.) A head down position often performed with spine surgery results in facial and orbital edema with increased venous pressure, especially after a prolonged surgery or associated with a large volume of intraoperative fluid replacement. (Alexandrakis G., et al., American Journal of Opthalmology, 27:354-355 (1999), the disclosure of which is incorporated herein by reference.) The prone position may contribute to increased orbital venous pressure from increased abdominal venous pressure, especially in patients who are overweight. Orbital venous pressure cannot easily be quantified. CT scanning of the orbit demonstrates grossly dilated superior ophthalmic veins and the dilatation of the venous plexus around the optic nerve and venous engorgement of the orbital apex, so positioning can be seen to have a contributing factor to the pathogenesis of perioperative ischemic optic neuropathy. Yet, there are case reports of patients who are not in a prone position who have developed this complication. Radical neck dissections, cesarean sections associated with anemia, nephrectomy, and cardiopulmonary bypass. Again, it is believed that this is a contributing factor, but it cannot be said to be an absolute causative factor.

Increased cerebrospinal fluid pressure may decrease arterial perfusion pressure and increase venous pressure, compressing the optic nerve vasculature. Direct measurement of this mechanism is lacking. However, after internal jugular vein ligation, the cerebrospinal fluid pressure can increase 100% following the unilateral ligation and 300% following bilateral ligation. (Schweizer O., et al., Annals of Surgery, 136:948-956 (1952), the disclosure of which is incorporated herein by reference.)

Dysfunction of the autoregulatory mechanism that maintains perfusion of the optic nerve head can result in increased resistance to blood flow. Autoregulation maintains a constant blood flow with fluctuations in perfusion pressure by modulating the resistance to blood flow through autonomic and vasoactive substances. (Arnold A. C., Journal of Neuroopthalmology, 23:157-163, (2003), the disclosure of which is incorporated herein by reference.) Proper autoregulation may be altered by arteriosclerotic disease resulting in decreased blood flow. Consequently, patients who experienced decreased perfusion pressure with arteriosclerotic disease may be at a greater risk for developing perioperative ischemic optic neuropathy. In one study, twenty out of twenty-eight patients with perioperative posterior ischemic optic neuropathy had one or more vascular risk factors for arteriosclerotic disease (hypertension, diabetes, tobacco use, hypercholesterolemia, coronary artery disease, congestive heart failure, cardiac arrhythmia, or cerebrovascular disease). (Sadda S. R., et al., American Journal of Opthalmology, 132: 743-750 (2001), the disclosure of which is incorporated herein by reference.) Unfortunately, in another study, no difference was found in the number of arteriosclerotic risk factors in patients who developed ischemic optic neuropathy after cardiopulmonary bypass as compared to a control group (except those patients who had clinically severe vascular disease or where clinically severe vascular disease was not defined). (Nuttall G. A., et al., Anest Anal G, 93:1410-1416 (2001), the disclosure of which is incorporated herein by reference.)

Direct ocular compression has been implicated in spinal surgery where patients are in the prone position utilizing a face support. However, direct ocular compression would tend to decrease intraocular perfusion pressure and appears to be associated more with central retinal artery occlusion than posterior ischemic optic neuropathy. There are a number of cases where this ischemic optic neuropathy has occurred in people who had their heads supported in a Mayfield headrest (Mayfield pins) where there was no direct ocular compression and the head was completely free.

Finally, it has been theorized that embolism could cause an increase in resistance to blood flow, but there was no evidence to support this mechanism occurring in posterior ischemic optic neuropathy. (Rizzo J. F., American Journal of Opthalmology, 103:808-811 (1987), the disclosure of which is incorporated herein by reference.) Also, embolism has not been noted during the funduscopic examination of patients with posterior ischemic optic neuropathy nor did any of the histopathological examinations reveal embolic phenomenon.

The case studies of perioperative ischemic optic neuropathy (ION) are also confused. Specifically, the histopathology of ION has been reported in three cases by Johnson in 1987, Marks in 1990, and Schobel in 1995. Johnson, et al., in 1987, reported a clinical pathological case of a fifty-nine year old woman who developed posterior ischemic optic neuropathy (PION) after an exploratory laparotomy, which was complicated by severe intraoperative hemorrhage and hypotension. She subsequently died from sepsis nine days after the onset of visual loss. Mild disk edema was found at the clinical examination, but at autopsy, the retrobulbar optic nerve was infarcted.

This case is included because it was thought that the disk edema resulted from the close proximity of the infarction to the optic nerve head. The gross neuropathological examination at autopsy revealed bilateral symmetric fusiform swelling and infarction with central intraparenchymal hemorrhage of the intraorbital portion of the optic nerve, worse on the right side. The remaining portion of the central nervous system was normal, including retina and intracranial visual pathways. Using serial sections, a composite diagram of the optic nerve was constructed. The infarcted segment coursed longitudinally and extended from the retrobulbar to the intracanicular portion bilaterally. The immediate retrolaminar area was spared bilaterally. The infarction predominantly affected the more central axial portion with sparing of the nerve periphery anteriorly and broadening posteriorly. In the mid-orbital section, the infarction extended into the periphery circumferentially and narrowed again posteriorly, ending at the optic canal.

Marks in 1990 reported a case of a sixty-seven year old man who had bilateral posterior ischemic optic neuropathy who died from sepsis fourteen days after a radical neck dissection that was complicated by intraoperative hypotension and anemia. (Marks S. C., et al., Head and Neck, 12:342-345 (1990), the disclosure of which is incorporated herein by reference.) The autopsy examination of the brain showed a fresh cerebral infarction that did not involve the occipital lobe. There was no indication of generalized cerebral edema. There was diffuse ischemia or watershed zone infarction.

Nawa, et al., in 1992, subsequently reported the optic nerve histopathology of this patient. (Nawa Y., Graefes Arch Clin Exp Opthalmol, 230:301-308 (1992), the disclosure of which is incorporated herein by reference.) The gross examination showed hemorrhagic infarction of the distal and proximal ends of the intraorbital portion of both optic nerves. The intraocular, intracanalicular, and intracranial portions were normal. The central portion of the optic nerve was infarcted with sparing of the peripheral fibers. Microscopic examination showed acellularity of the fiber vascular pial septae, mild hemorrhage, glitter-cells (swollen macrophages), infiltrate, and loss of myelin. A few small thrombi in the paracentral pial vessels were found, but no emboli were observed. No abnormalities were detected in either eye.

Finally, Schobel reported, in 1995, the clinicopathological case of a forty-eight year old man with bilateral posterior ischemic optic neuropathy, which occurred after bilateral neck dissection for squamous cell carcinoma of the mouth. (Schobel G. A., et al., Int J Oral Maxillofac Surg, 24:283-287 (1995), the disclosure of which is incorporated herein by reference.) This surgery was complicated by hypotension and blood loss. Six months later, the patient had partial visual acuity of the left eye with a severely constricted visual field. One year later, the patient died from generalized metastasis and at autopsy there was no evidence of cerebral infarction. The histopathology of the intraorbital optic nerve showed complete loss of axons on the right and loss of the peripheral axons with sparing of the central axons on the left. The loss of peripheral axons appear to correspond to the constricted visual field.

Based on this histopathology it would appear obvious that hemodynamic derangement must play a role in the cause of ischemic optic neuropathy, but all individuals are equally susceptible. The fact that the intraorbital optic nerve is selectively infarcted and the remaining central nervous system is spared suggests that there is something unique about the optic nerve and it is more susceptible to the effects of hemodynamic derangements in some patients.

Figure 9:
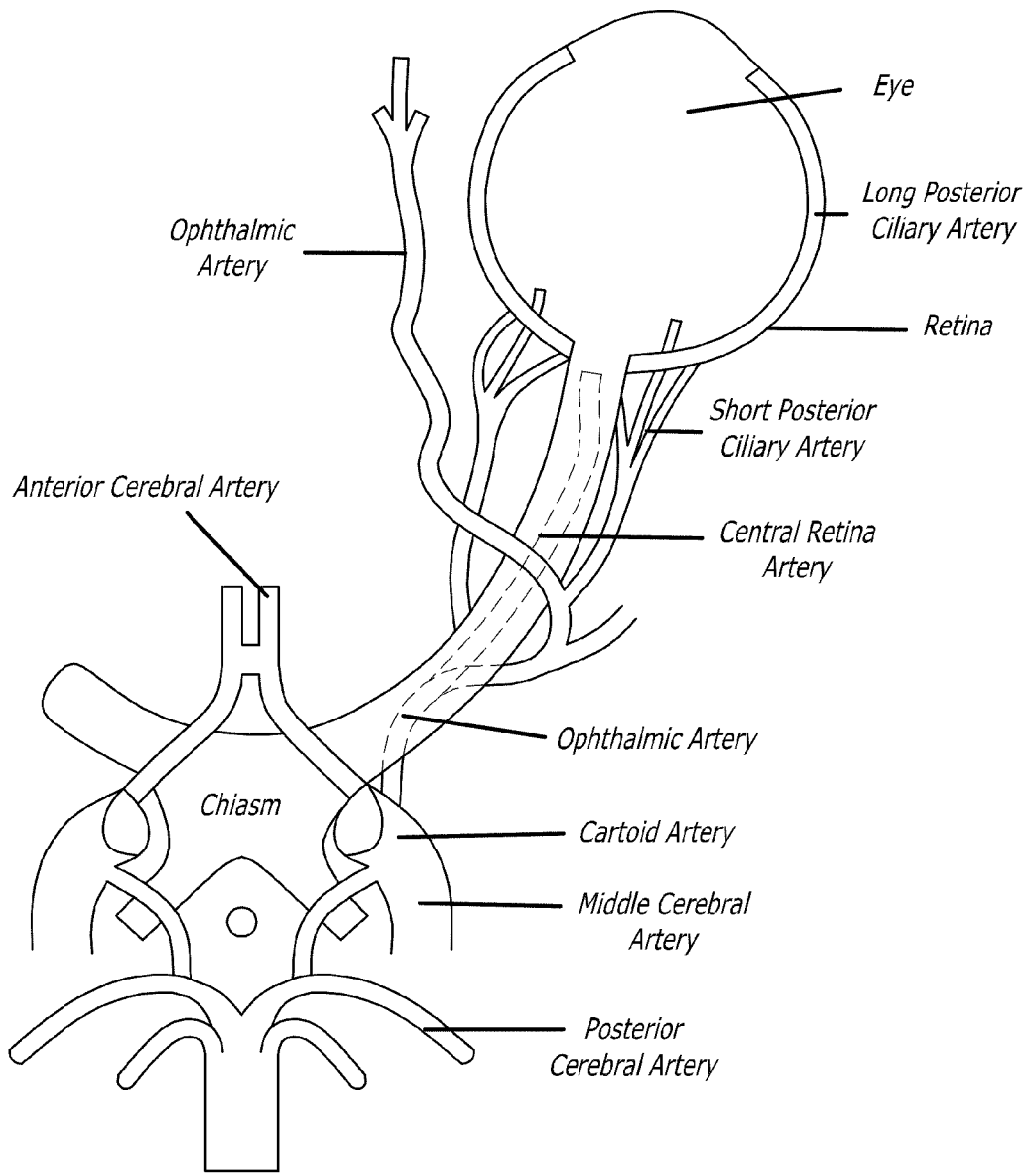
FIG. 9 provides a schematic diagram of the blood vessels associated with the eye.

There are a number of unique facts about the blood supply of the optic nerve, which will be discussed in reference to FIG. 9, that it is now believed might make the optic nerve particularly susceptible to such hemodynamic derangements. Firstly, it enters at an oblique angle into the optic nerve and as it enters the meningeal covering of dura and pia, the histological arrangement of the blood vessel changes. The walls become less "muscular" and the blood vessel becomes more fragile. The dura is known to have redundancy and "bagginess" around the optic nerve. In the prone position, the weight of the eye and muscular relaxation could cause traction on the optic nerve. In this situation, traction on the fragile central retinal artery would decrease the diameter of the blood vessel and reduce the perfusion to the optic nerve.

When you consider the histopathology, it would appear that there are two separate systems of blood supply to the optic nerve. There is a pial plexus, which surrounds the periphery of the nerve and penetrates the nerve a variable distance. The pial plexus is derived from collateral branches arising from the ophthalmic artery. The axial system is formed from small branches from the central retinal artery. There appears to be considerable anatomic variation in the number of anastomoses between the peripheral centripetal system and the axial centrifugal system in the intraorbital optic nerve because there are no anastomoses between the two systems and endartery formation occurs creating a watershed zone, which may be the reason that this section of the nerve is more vulnerable. (Awai T., Jpn J Opthalmol, 29:79-98 (1985), the disclosure of which is incorporated herein by reference.)

Poiseuille's Law states that "the resistance to blood flow is inversely proportional to the fourth power of the radius of the vessel and is directly proportional to blood viscosity and the length of the vessel". Here is the mechanism where the autoregulation of perfusion of the optic nerve head is deranged. One of the other factors is that, as will be discussed further below, this condition appears to be associated with long procedures, large amounts of blood loss, and replacement of blood with crystalloid, as opposed to colloid, or whole blood, may be the answer to the riddle of posterior ischemic optic neuropathy. A decrease in gradient of blood flow in the optic nerve from the prelaminar region to the optic chiasma was seen in the cat model. (Weinstein J. M., et al., Invest Opthalmol Vis Sci, 24:1559-1565 (1983), the disclosure of which is incorporated herein by reference.) Such a gradient would make the nerve more susceptible to the effects of hemodynamic derangement.

Figure 10:
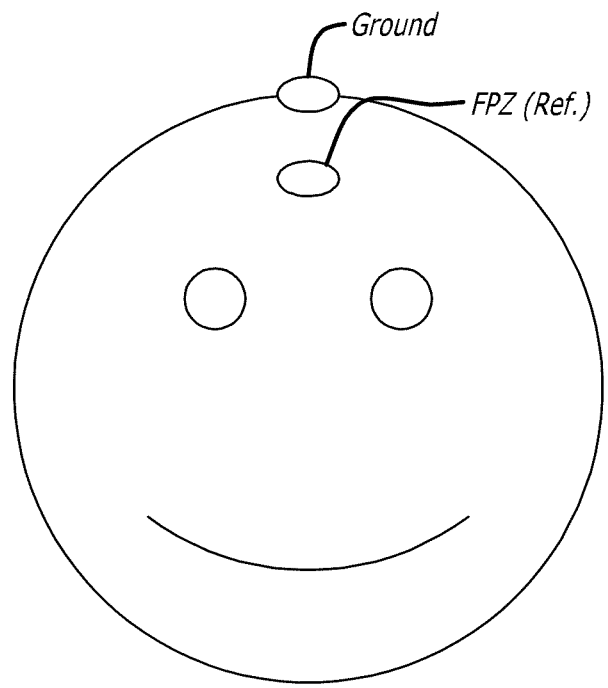
FIG. 10 provides schematic diagrams showing one exemplary method of placing electrodes for using in monitoring visual evoked potentials in accordance with the current invention.
Figure 10:
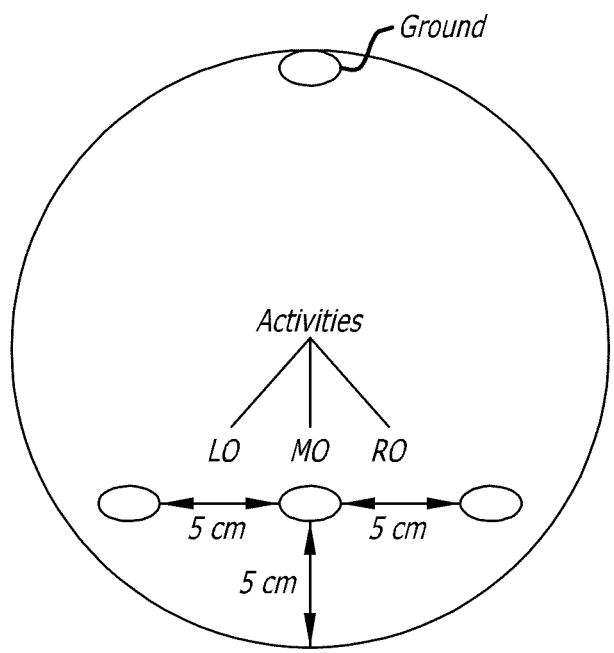

Anecdotal evidence for linking POVL to hemodynamic problems can also be found by examining studies conducted on the results of aging on the optic nerve. However, before reviewing the results of the studies, it is important to understand the anatomy of the optic nerve. As shown in FIG. 10, the optic nerve is a central nervous system fiber tract invested by pia mater, arachnoid, and dura mater, and is divided into bundles by fibrous glial septa, which run the nutrient vessels. The central artery of the retina enters the nerve about 1 cm from the nerve head. (Hayreh S. S., British Journal of Opthalmology, 47:651-662 (1962) the disclosure of which is incorporated herein by reference.) The nerve near the globe differs from the more proximal portion by containing the central retinal vessels in the middle. It is also larger in cross-section and has broader connective tissue components. The arteries within the dural sheath have the thin muscle coat and internal elastica of cerebral vessels, while those outside have sturdier structure of systemic arteries with more muscle and elastic tissue, which makes the optic nerve vulnerable to axial traction injuries (Poiseuille's Law). The myelin is of the central type and is contributed by the glia oligodendroglia. The other glial cells are microglia and astrocytes. Nerve fibers cross the sclera at the cribriform plate and become myelinated proximal to it.

Dolman in 1980 analyzed three hundred optic nerves from age of birth to 96 years and compared the size of the nerves calculating the area of cross-section. (Dolman C. L., et al., Archives of Opthalmology, Volume 98, 2053-2058 (1980) the disclosure of which is incorporated herein by reference.) The longest and shortest diameters within the pia mater were measured with a micrometer. The figures were averaged for each nerve and the cross sectional area was calculated from the formula for cross-sectional area (cross-sectional area=$\pi R^2$). The nerve was seen to be round in the orbital portion and then became oval as it entered the cranial cavity. There was a retrobulbar enlargement, which was approximately one-eighth greater than at the midpoint of the nerve. The cross-section diameters are demonstrated in Tables 3 and 4 below, and were smaller than diameters calculated by Sylvester and Ari. However, the difference may be explained by the fact that in the Dolman series, the nerves were trunk by the paraffin treatment of the sections (see Table 1).

TABLE 3

Average Area of Cross Section of Optic Nerves

| Dolman et al. | | Sylvester and Ari | |
| --- | --- | --- | --- |
| Age | Area (sq. mm) | Age | Area (sq. mm) |
| 0-6 mo | 2.8 | 0-6 mo | 4.27 |
| 3-4 yr | 5.4 | 3-4 yr | 9.12 |
| 7-10 yr | 6.25 | 7-10 yr | 9.76 |
| 15-55 yr | 6.75 | Adult | 9.93 |
| 60-96 | 6.75 | — | — |

This data shows that the optic nerve is quite small at birth, but grows rapidly during the first years after which the growth rate slows. The adult size is achieved at between 12 and 15 years. The size remains constant thereafter. Sylvester and Ari in 1961 used a special gauge and measured thirty premature and mature infants, as well as 180 other patients. (Sylvester P. E., et al., Journal of Neurology, Neurosurgery, and Psychiatry, 24:45-59 (1961) the disclosure of which is incorporated herein by reference.) Their figures demonstrated a doubling in size of the optic nerve between birth and the age of 3 to 4 years and then a much slower increase in size. They believe that adult size was attained at age 12 years. These anatomical changes are also seen in laboratory rats. There was little change in the cross-sectional diameter between birth and five days. Maximal change occurred between five and ten days. Very little change occurred in diameter between ten and twenty days. The adult optic nerve size in a rat is achieved at fifty days.

Observations were also made concerning the connective tissue around the optic nerve. These are summarized in Table 4, below.

TABLE 4

Average Thickness of Fibrous Tissue Components

| | Thickness (µm) | | |
| --- | --- | --- | --- |
| Age | Dura mater | Pia mater | Septa |
| 1 mo | 93.8 | 18.8 | 0.9 |
| 1 yr | 187.6 | 46.9 | 9.4 |
| 4 yr | 234.5 | 46.9 | 11.2 |
| 15-55 yr | 375.2 | 46.9 | 14.1 |
| 60-96 yr | 35.2 | 93.8 | 28.1 |

The thickness of the dura and pia mater were measured with a micrometer. The dura mater doubled in thickness during the first year and doubled again from that point on to adulthood. Pia mater, fine at birth, doubles in thickness by one year and then gradually becomes heavier. The septa, which divide the optic nerve, are extensions of the pia mater and reach into the substance of the nerve. The lamina cribrosa is very rich in elastic fibers. In childhood and in the prime of life, the optic nerve is closely packed with more than one million axons. (Hughes A., et al., Journal of Comp Neurology, 169: 171-184 (1976) the disclosure of which is incorporated herein by reference.)

Oppel in 1963 counted 1,186,172 myelinated fibers in the optic nerve of a thirty-year-old healthy man; 21,351 were large and 69,984 were medium sized and 1,094,837 were small. (Oppel O., Albrecht Von Graefes Arch Klin Exp Opthalmol, 166:18-27 (1963) the disclosure of which is incorporated herein by reference.) From the age of sixty onwards, many nerves display diminishing density of axons. Brabec in 1977 reported the presence of swollen axons in the nerve head at the level of the cribriform plate in individuals from the age of forty-six on to eighty years. (Brabec F., Albrecht Von Graefes Arch Klin Exp Opthalmol, 200:231-236 (1977) the disclosure of which is incorporated herein by reference.) The numbers increased in aged persons. Swelling of axons may be due to ischemia. The optic nerve at the level of the lamina cribrosa and proximal to it is particularly apt to suffer ischemic damage in the elderly because of insufficient perfusion through the posterior ciliary arteries. (Hayreh S. S., AMALRICP, Editor of Proceedings of the International Symposium on Fluorescein and Geography, Albi, 1969, Switzerland; S Karger AG, 510-530 (1971) the disclosure of which is incorporated herein by reference.)

Glaucoma contributes to ischemia of the retrobulbar portion of the optic nerve and initiates marked axonal swelling. (Lampert P. W., et al., Invest Opthalmol, 7:199-213 (1968) the disclosure of which is incorporated herein by reference.) Dolman, in 1980, demonstrated vascular degeneration, hyalinization of the arterioles, intimal fibrosis, and elastosis of small arteries, which were common in their series and were always associated with the history and autopsy finding of vascular disease. (Dolman C. L., et al., Archives of Opthalmology, Volume 98, 2053-2058 (1980) the disclosure of which is incorporated herein by reference.) Thirty of the three hundred subjects had focal scars with complete loss of axons astrocytic gliosis and marked thickening of the septa. All of those patients had generalized arterial sclerosis.

Likewise, Schnabel's cavernosa degeneration has been attributed to several causes, but particularly to glaucoma and vascular disease. (Henkind, 1976, Lampert, 1968, Virchow K, 1972 (cited), "Anatomy and Pathology of the Optic Nerve Head in Glaucoma", Trans-Am Acad Opthalmol Otolaryngol, 81:192-196 (1976) the disclosure of which is incorporated herein by reference.) Cavernosa degeneration involved a segment of the cross-section of the nerve beginning at the cribriform plate and projecting backwards for a distance of five millimeters. The nerve beyond that showed tract degeneration.

In addition, with increasing age, the fibrous tissue covering and intersecting the optic nerve broadens and coarsens, and the elastic tissue multiplies. Eventually, the nerve is encased in a sleeve of leptomeninges and wrinkled dura mater. The fibrous septa encroach on the area occupied by the nerve fibers and yet the nerve remains the same size. The fiber bundles become rarified as age increases. Horgan and Zimmerman in 1962 suggested that the condensation of fibrous tissue of the septa impeded the diffusion of nutrients from the vessels to the axons and thus caused the axonal depletion. (Horgan M. J., et al., Zimmerman L E, "The Optic Nerve in Ophthalmic Pathology, Second Edition", Philadelphia, WB Saunders Company, 1962; 577-580 the disclosure of which is incorporated herein by reference.) However, Dolman, et al., did not see a direct relationship between the width of the septa and the density of the axons within the fiber bundles. (Dolman C. L., et al., Archives of Opthalmology, Volume 98, 2053-2058 (1980) the disclosure of which is incorporated herein by reference.) They postulated an alternative explanation based on the frequent presence of swollen axons at the nerve head pointing to local injuries sustained by the axons in this area. A block to axoplasmic flow at this level had been postulated by Brabec in 1977. (Brabec F., Albrecht Von Graefes Arch Klin Exp Opthalmol, 200:231-236 (1977) the disclosure of which is incorporated herein by reference.) Wirtschafer, in 1977, experimentally stopped axoplasmic flow and produced axonal swellings filled with cell organelles in the nerve head by proximal ligature of the optic nerve. In man, the swelling of axons in this particular area may be due to anoxic damage caused by faulty perfusion through aging sclerotic vessels in a watershed zone caused either through glaucoma or simply old age. (Wirtschafer J. D., et al., Invest Opthalmol, 16:537-541 (1977), the disclosure of which is incorporated herein by reference.) For additional information see the following additional references Armaly M. F., et al., Invest Opthalmol, 14:475-479 (1975) ; Birchow K., cited by Austin J. H., "Corpora Amylacea" in Minckler J, Editor, Pathology of the Nervous System, New York, 1972, Volume 111:2961-2968; and Hayreh S. S., "The Pathogenesis of Optic Nerve Lesions in Glaucoma", Trans-Am Acad Opthalmol Otolaryngol, 81:197-213 (1976), the disclosure of which are incorporated herein by reference.)

Surgical Procedures Implicated

In short, there have been numerous studies on ION disorders that have implicated any number of physiological conditions. (See, e.g., Chutkow J. G., et al., Mayo Clin Proc, 48:713-717 (1973) ; Harris A., et al., Opthalmol, 116:1491-1495 (1998) ; Hayreh S. S., Indian Journal of Opthalmology, 48:171-194 (2000) ; Johnson M. W., et al., Opthalmology, 94:1577-1584 (1987) ; Lee L. A., et al., Anesthesiology, 95:793-795 (2001); Orgul S., et al., Surv Opthalmol 43, Supplemental 1, S17-S26 (1999) ; Roth S., et al., "Injuries to the Visual System and Other Sense Organs in Saidman L, Editor", Anesthesia and Perioperative Complications, Edition Two, St. Louis, Mosby, 1999; Sugarbaker E., et al., Cancer, 4:242-250 (1951) ; and Tobin H. A., Laryngoscope, 82:817-820 (1972), the disclosures of which are incorporated herein by reference.) Moreover, perioperative visual loss is known to occur in cases, such as cardiopulmonary bypass, renal surgery where there were large amounts of blood loss, head and neck surgery, and neurosurgery. However, spine surgery seems to pose the greatest risk for postoperative visual loss. (See, e.g., Huber J. F., et al., Spine, 23:1807-1809 (1998) and Katz D. A., et al., Spine, 30:E83-E85 (2005), the disclosures of which are incorporated herein by reference.) The risk of visual loss following spine surgery is ten times greater than the risk of visual loss following opthalmological surgery. Complications are reported associated with supine and lateral positioning, but there is a ten-fold increase in eye injuries with prone spine surgical procedures. Indeed, in 1948 Slocum reported the first case of blindness resulting from the prone position during spine surgery. (Slocum H. C., et al., Surgery Gynecology and Obstetrics, 1948, 86:729-732, the disclosure of which is incorporated herein by reference. In that case blindness was caused by malpositioning of the head on a Bailey headrest. (Myers M. A., et al., Spine, 22:1325-1329 (1997), the disclosure of which is incorporated herein by reference.) In 1954, Hollenhorst, et al. reported blindness caused by prone positioning with the Mayfield horseshoe headrest. (Hollenhorst R. W., et al., Archives of Opthalmology, 52:819-830 (1954), the disclosure of which is incorporated herein by reference.) These authors expressed their opinion that increased intraocular pressure was the principle pathophysiology resulting in visual loss. They thought the problems were caused by periorbital pressure from the horseshoe headrest. They went on to evaluate 198 patients who had vision loss, which was described "as distant hemorrhage". They established the association of hypoperfusion as being the key etiological factor.

Despite the fact that there has been a long and growing body of evidence that opthalmological complications are associated with a variety of surgical procedures and positions, there are some remarkable conflicts in the data concerning incidents of perioperative visual loss. For example, Roth, et al. reviewing 60,965 consecutive patients who underwent general anesthesia for non-opthalmological surgery found no patients with postoperative visual loss. (Roth S., et al., Anesthesiology, 1996, 85:1020-7, the disclosure of which is incorporated herein by reference.) Stephens reviewed 3,450 spine surgeries in a nine-year period and found only three patients who had postoperative visual loss for an incidence of 0.087%. (Stephens W. R., et al., Spine 22:1319-24, 1997, the disclosure of which is incorporated herein by reference.) Balm, et al. evaluated 1,200 neck dissections and found only one patient, 0.08%, who had visual loss in the postoperative period. (Balm A. J., et al., J. Laryngol. Otol. 104:154-6, 1990, the disclosure of which is incorporated herein by reference.) Likewise, Maran in 1989 analyzed his nineteen year experience of radical neck dissection reported no patients who had visual loss. (Maran A. G., et al., J. Laryngol. Otol. 103:760-4, 1989, the disclosure of which is incorporated herein by reference.) Despite these apparent low incident rates, a recent survey by the Scoliosis Research Society indicated that one eye complication occurred for every one hundred spine procedures. Ischemic optic neuropathy is second only to glaucoma as a cause of blindness. The incidence varies from 0.01% to 1%. (See, e.g., Roth S., et al., cited above; Warner M E, 2001; Williams E L, 1995; Kumar N, 2004) . However, other studies indicate that the incidence may be as high as 4.5%. (See, Shaw P. J., et al., "Neuroopthalmological Complications of Coronary Artery Bypass Graft Surgery", ActiNeural Scan-D 76:1-7 (1987), the disclosure of which is incorporated herein by reference.)

It is possible that the acknowledge incidence rate is low because of under reporting. Since the American Society of Anesthesiology Visual Loss Registry was established in 1999, there has been a growing awareness and an increase in reporting of this complication, which suggests that it may actually be far more common than was previously suspected. In general, the strength of the data that has been collected so far is quite weak, hence the great disparities on the percentage incidence of this complication. However, by the last days of June of 2005, ninety-three cases of perioperative visual loss associated with spine surgery had entered the American Society of Anesthesiology Postoperative Visual Loss Registry. They constituted that this was 72% of the total number of one hundred thirty-one cases. From these results it was clear that prone spine surgery is clearly the most common procedure associated with postoperative visual loss. The analysis of the cases showed that ischemic optic neuropathy was the cause of visual loss in 89% of the ninety-three spine cases. Fifty-six cases were diagnosed as posterior ischemic optic neuropathy and nineteen were diagnosed as anterior ischemic optic neuropathy. Eight cases were diagnosed as unspecified ischemic optic neuropathy. The results are summarized in Table 5, below.

TABLE 5

POVL Ophthalmic Lesion Associated with Spine Surgery

| Ophthalmic Lesion | Cases (%) | No light Perception (%) |
|---|---|---|
| ION | 83 (89) | 47 (57) |
| PION | 56 (60) | 34 (61) |
| AION | 19 (20) | 8 (42) |
| ION unspecified | 8 (9) | 5 (63) |
| CRAO | 10 (11) | 7 (70) |

AION: anterior ischemic optic neuropathy
CRAO: central retinal artery occlusion
ION: ischemic optic neuropathy
PION: posterior ischemic optic neuropathy In a demographic analysis of the eighty-three spine surgery cases, which had ischemic optic neuropathy, there were significantly more males than females (72% males and 28% females). The mean age was fifty years, plus or minus fourteen years, the range being between sixteen and seventy-three years. Most patients were seen as being relatively healthy with 64% of the patients being rated in the American Society of Anesthesiology Physical Status Levels as a Class I or Class II and 96% of the patients were undergoing elective surgery. Coexisting diseases included hypertension, diabetes, the use of tobacco, coronary artery disease, cerebrovascular disease, elevated cholesterol or lipids, and obesity. At least one of these factors was present in 82% of all of the cases. In the 41% of the patients who were hypertensive, thirteen were being treated with beta blockers, eleven used angiotensin converting enzyme inhibitors, eleven used calcium channel blockers, and eleven used diuretics, and five used other or unknown medications. Not one patient had a preoperative history of glaucoma.

All of the patients were positioned prone for a portion of the procedure, except for two anterior spine procedures. Ten procedures involved a supine lateral and prone position, i.e. combined anterior and posterior procedures. Some of the patients were positioned on the Wilson frame, some were positioned on a Jackson table, and some were positioned on soft chest rolls. The headrests that were used most commonly were foam pads, but there were patients immobilized in Mayfield pins and/or donut/gel pads. Eyes were checked routinely throughout the surgery and were documented by the anesthesiologists in 51% of the cases.

Of the eighty-three patients who had ischemic optic neuropathy, 66% had documented bilateral involvement for a total of one hundred thirty-eight affected eyes. The median onset time of reporting visual loss postoperatively was fifteen hours, the range being from zero to one hundred sixty-eight hours following surgery. One patient who was mechanically ventilated for two weeks postoperatively reported complete blindness two days after his extubation.

Full or partial eye opening was noted immediately post-op in forty-three patients. The inability to open one or both eyes was noted in twelve patients and the ability to open the eyes was missing from the anesthesia records of twenty-eight patients.

There was associated periocular trauma in one case. Visual fields were restricted in one hundred thirty-four of one hundred thirty-eight affected eyes. Complete blindness with loss of light perception occurred in sixty-four of the one hundred thirty-eight affected eyes (forty-seven patients).

Posterior ischemic optic neuropathy was diagnosed in 67% of all of the ischemic optic neuropathy cases. Anterior ischemic optic neuropathy was diagnosed in 23% of the cases. Unspecified ischemic optic neuropathy was diagnosed in 10% of the cases. There was some degree of recovery of vision in 42% of the ischemic optic neuropathy cases, although improvement was often clinically insignificant, i.e. the patient could tell the difference between light and dark or had a perception of hand motion only. Follow up opthalmological examinations appeared to be inconsistent in this study group. It varied from an initial examination to one four years post-op.

In the spine surgery cases where the patient had central retinal artery occlusion, which numbered ten patients, the mean age was 46 years (plus or minus thirteen years). Horseshoe headrests were used in three cases, foam pads were used in two cases, and miscellaneous headrests were used in five cases. Mayfield pins were not used in any of the central retinal artery occlusion cases in contrast to 19% of the ischemic optic neuropathy cases. Eye checks were performed in six of the ten cases at intervals from thirty minutes to only once during a ten-hour case. Mean anesthetic duration and the mean blood loss were less in the central retinal artery occlusion cases. Deliberate hypotension was utilized in four of the ten central retinal artery occlusion cases. There were no cases of bilateral central retinal artery occlusion, however, the recovery of vision between central retinal artery occlusion and ischemic optic neuropathy groups were not significantly different. Periocular trauma was documented in seven of the ten central retinal artery occlusion cases compared to only one of the eighty-three ischemic optic neuropathy cases. These included ipsilateral findings of decreased supraorbital sensation, opthalmoplegia, corneal abrasion, ptosis, and/or unilateral erythema. (For additional information see, e.g., Horan F. T., Journal of Bone and Joint Surgery, British, 87:1589-1590 (2005); Kumar R. N., et al., American Journal of Opthalmology, 138:889-91 (2004); and Stambough J. L., et al., Journal of Spinal Disorders, 363-365 (1992), the disclosures of which are incorporated herein by reference.)

Risk Factors

An eighteen-member panel of the American Society of Anesthesiologists met, chaired by Mark A. Warner, M.D. of Rochester, Minn., and submitted for publication on Nov. 2, 2005 their recommendations concerning postoperative visual loss. (American Society of Anesthesiologists Postoperative Visual Loss Registry, Analysis of 93 Spine Surgery Cases, Laurie Lee, M.D., et al., Anesthesiology V. 105, No. 4, October 2006:652-659, the disclosure of which is incorporated herein by reference.) Attached in Appendix A are the tables of data that they generated and the consensus that was developed from their deliberations. The panel identified that preoperative anemia, vascular risk factors, such as hypertension, glaucoma, carotid artery disease, smoking, obesity, and diabetes, were associated with perioperative visual loss. Also associated was substantial blood loss and prolonged surgical procedures.

Procedures were thought to be prolonged when they exceeded 6.5 hours (range of 2 to 12 hours.) They also considered blood loss to be substantial when it achieved a point of being 44.7% of the estimated blood volume (the range was 10 to 200%.) They made recommendations concerning blood pressure management, management of intraoperative fluids, management of anemia, management of vasopressors, patient positioning, and surgical procedures.

In the American Society of Anesthesiology Study in 2005, eighty-three of the ninety-three cases were ischemic optic neuropathy. It is more probable in males than females (72% male and 28% female). The mean age was fifty years, plus or minus fourteen years. The range was sixteen to seventy-three years. The majority of the patients were healthy, ASA Class I or II, and 96% were undergoing elective surgery.

As mentioned, coexisting diseases included hypertension, diabetes, tobacco use, coronary artery disease, cerebrovascular disease, increased cholesterol, lipids, and obesity were present in between 4 to 53% of the cases. At least one condition was present in 82% of the cases. Of the 41% of the hypertensive patients, thirteen used beta-blockers, eleven used angiotensin converting enzyme inhibitors, eleven used calcium channel blockers, eleven used diuretics, and five used something else. Not one patient had a preoperative history of glaucoma.

In spinal cases, the following risk factors were found:
  89% of cases with ischemic optic neuropathy underwent surgery for fusion with or without instrumentation for more than one vertebral level in the thoracic, lumbar, or sacral region.
  One-third (39%) had previous spine surgery.

All of the patients were positioned prone for a portion of the procedure, except two had anterior spine procedures and ten had procedures, which involved supine or lateral and prone positions.

Approximately one-third used a Wilson frame, one-third used the Jackson table, and one-third used soft chest rolls. The headrests most commonly used were foam pads, Mayfield pins with the Mayfield headrest, and donut or gel pads.

The majority of the cases (94%) were greater than six hours or longer in duration. The median blood loss was 2.0 liters. The range was 0.1 to 25 liters of blood; 82% of the cases had an estimated blood loss of 1.0 liters or greater.

Fluid management varied with colloid use in 30% of the cases. Blood was replaced with a cell saver in 54% of the cases. Packed erythrocytes were used in 57% of the cases. Whole blood was used in 11% of the cases.

Urine output was less than 0.5 ml per kilogram in one-quarter of the cases. Postoperative increased creatinine occurred in six cases and rhabdomyolysis occurred in three cases.

Blood pressure varied; in 33% of the cases, the lowest blood pressures were greater than ninety millimeters mercury, 20% had the lowest systolic blood pressure of eighty milligrams of mercury or less, 6% of the cases had the lowest mean arterial blood pressure, which was less than 20% below baseline, and 34% of the cases had a systolic blood pressure 40% or greater below the baseline. Deliberate hypotension was utilized in 27% of the cases.

Summary

In summary, it is proposed that blood flow in the posterior optic nerve is susceptible to increased venous pressure because the arterial supply to the posterior optic nerve is derived from small end vessels from the surrounding pia. There are case reports of ischemic optic neuropathy that occurred in patients associated with increased venous and intracranial pressure after radical neck operations with bilateral jugular vein ligation. In the current invention the conclusion has been drawn from this that high venous pressure and interstitial tissue edema can compromise blood flow in the optic nerve.

The histopathological studies of posterior ischemic optic neuropathy in one patient associated with severe blood loss and in two patients who had bilateral radical neck dissections demonstrated central hemorrhagic infarction several millimeters posterior to the lamina cribrosa all of the way up to several millimeters anterior to the optic nerve canal. This is an area that is supplied by the small pial blood vessels. Accordingly, although not to be bound by theory, it is believe that ischemic optic neuropathy might be caused by increased venous pressure and/or interstitial fluid accumulation within a nondistensible space, either the lamina cribrosa at the optic nerve head or the bony optic canal. Furthermore, the increase in volume of the eye due to venous engorgement increases the traction and the mass of the eye as it "prolapses" or descends. This in turn provides traction and alteration of the caliber of the blood vessels perfusing the optic nerve, aggravating this watershed vascular supply in the optic nerve structure.

The current invention recognizes that it is the combination of these two mechanisms that is the probable origin of ischemic optic neuropathy in surgical patients, and particularly in spinal surgery patients. Specifically it should be recognized that:

ION always occurred without any evidence of vascular injury. Optic nerve vasculature is uniquely vulnerable to hemodynamic alterations in the prone position.

72% of cases were sine surgery in the prone position.

89% of cases were associated with ischemic optic neuropathy and were relatively healthy.

Estimated blood loss of 1,000 ml or greater and surgery lasting over six hours was present in 96% of the cases.

As such, it is submitted that current techniques are insufficient to monitor and diagnose potential cases of POVL in real-time. Specifically, current standards do not provide monitoring of the function of the optic nerve or the rate of perfusion of blood into the optic nerve. Indeed, current methodology only requires monitoring of the fluid and pressure of the patient as a whole. However, as discussed above the optic nerve is uniquely susceptible to damage while under anesthesia, and particularly in a surgical environment. Accordingly, the current invention, which allows for the monitoring of neurological optic function through a VEP sensor and vascular function through a combination of an intraocular pressure sensor and a blood flow sensor, would uniquely allow for the monitoring and diagnosis of the major risk factors of POVL in real-time.

More specifically, by providing a physician with real-time information about hematological information about blood flow and perfusion into the eye through the intraocular pressure and blood flow sensors, in combination with an ability to monitor how the optic nerve is function neurologically through the VEP sensor, the current invention allows a physician to get a clear picture of the ongoing function and health of the optic nerve. In a case where the monitor of the current invention detects a decrease in blood flow to the eye in combination with an alteration in neurological function of the optic nerve, the physician would be alerted and provided sufficient information to determine what, if any, counter measures might be employed to prevent possible damage the optic nerve.

Proposed Test Procedure

The current invention proposed the use of VEPs to monitor optic function. In operation of the invention, goggles containing light-emitting diodes (LEDs) will be placed on a patient in one of either a sleeping, coma or sedated state. The LEDs will be programmed to stimulate VEPs in the patient. Electrodes, either gold cupsa, disposable subdermal needles or sticky leads, will be placed on the patient's head, as shown in FIG. 10. In short, a reference electrode is placed in the forehead (12 cm above the nasion) and is labeled FPZ. A ground electrode is placed on the top of the head. The active electrode is placed at the back of the head at the mid-occipital (MO) scalp region. This MO electrode is placed 5 cm from the inion. In the preferred method, another electrode is placed 5 cm to the right of the MO and another 5 cm to the left of the MO. These two additional electrode are labeled left occipital (LO) and right occipital (RO), as shown in the figure.

The LED goggles will be place over the patient's eyes and using the VEPS generated from the stimulus the P100 cortical response with be monitored. Changes in the P100 will be noted and relayed to the surgeon and anesthesiologist. As discussed, patients undergoing operation in the prone or supine position can be vulnerable to visual impairments and blindness. Case studies have shown that after undergoing a surgical procedure patients complain of visual disturbances in one or both of the eyes. These impairments can last a few hours up to a few days or longer. Monitoring the visual pathways with the system should show changes in the P100 response if the cortical response is degraded or impaired while the patient is under anesthesia. These changes will be used to alert the surgeon and anesthesiologist to make the necessary adjustments to the medications or fluids being administered, or to make positional adjustments to the patient's head or body on the operating table, or to consider the possibility of terminating the procedure to prevent the probability of a service post-op complications.

Example 2

Anesthesia Awareness

Anesthesia awareness, or "unintended intra-operative awareness" occurs during general anesthesia, when a patient has not had enough general anesthetic or analgesic to prevent consciousness. There are two states of consciousness that may be present:
- Awareness. When patients seem to be vigilant and cognizant responding to commands but with no postoperative recall or memory of the events.
- Memorization and recall. When patients can recall events postoperatively but were not necessarily conscious enough for responding to commands.

The most traumatic case of anesthesia awareness is full consciousness during surgery with pain and explicit recall of intraoperative events. In less severe cases, patients may have only poor recollection of conversations, events, pain, pressure or of difficulty in breathing. The experiences of patients with anesthesia awareness vary widely, and patient responses and sequelae vary widely as well. This experience may be extremely traumatic for the patient or not at all. Indeed, some patients experience posttraumatic stress disorder (PTSD), leading to long-lasting after-effects such as nightmares, night terrors, flashbacks, insomnia, and in some cases even suicide.

Recently attempts have been made to manufacture awareness monitors. Typically these monitor the EEG, which represents the electrical activity of the cerebral cortex, which in theory is active when awake but quiescent when anaesthetized (or in natural sleep). However, none of these systems are perfect. For example, they are unreliable at extremes of age (e.g. neonates, infants or the very elderly). Secondly, certain agents, such as nitrous oxide, ketamine or xenon may produce anesthesia without reducing the value of the depth monitor. This is because the molecular action of these agents (NMDA receptor antagonists) differs from that of more conventional agents, and they suppress cortical EEG activity less. Thirdly, they are prone to interference from other biological potentials (such as EMG), or external electrical signals (such as diathermy). Finally, because the cortex is active at all times there is significant background. This means that the technology does not yet exist which will reliably monitor depth of anesthesia for every patient and every anesthetic.

Figure 11:
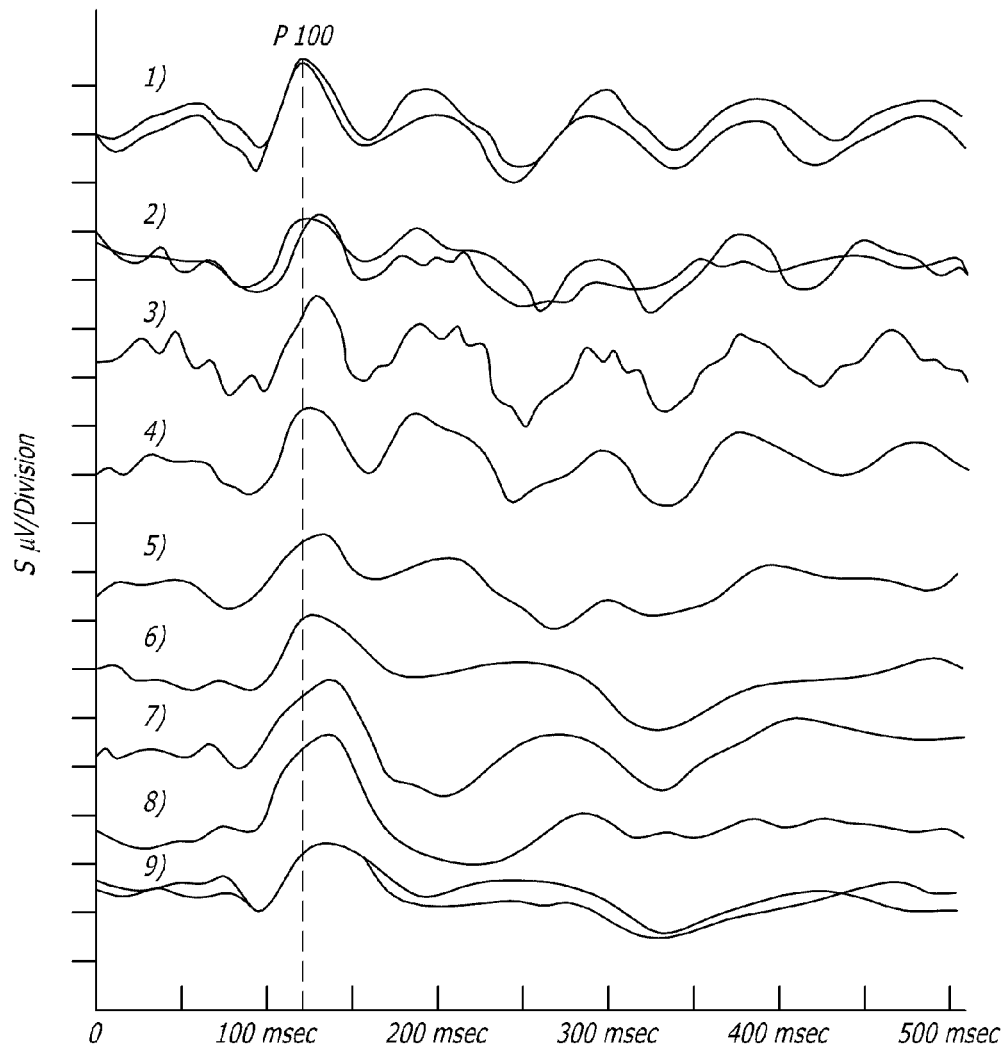
FIG. 11 provides waveforms taken while monitoring the P100 cortical response while under anesthesia.

It is well known that during surgery, the large amounts of anesthetic gases used can affect the amplitude and latencies of VEPs. Any of the halogenated agents or nitrous oxide will increase latencies and decrease amplitudes of responses, sometimes to the point where a response can no longer be detected. Indeed, several studies have shown that changes in cortical responses can be affected by several factors, including anesthetic agents and surgical stimuli. (Chi, O., et al., Anesthesiology, 67:827-830 (1987), the disclosure of which is incorporated herein by reference.) For example, Uhl, et al., have demonstrated a change in latency and amplitude due to anesthesia. They demonstrated that the P100 latency was prolonged by halothane. (Uhl, R. R., et al., Anesthesiology, 53:273-276 (1980), the disclosure of which is incorporated herein by reference.) Likewise, Burchiel, et al., showed that the amplitude of the VEP was increased at high concentration of enflurane (2.5-3.7%). (Burchiel, K. J., et al., Electroencephalo. Clin. Neurophysiol., 39:434 (1975), the disclosure of which is incorporated herein by reference.) Chi, et al. also showed that nitrous oxide anesthesia slightly increased the latency of the VEP with no significant change in amplitude. (See for example the time-lapse measurements taken in FIG. 11, showing the decrease in number of peaks as a patient is placed under anesthesia.)

Because the P100 cortical response is the biggest and most consistent to monitor, it is proposed that in accordance with the current invention using the optic function monitor described herein can be used to measure the P100 cortical response from VEPs to determine the awareness of a patient under anesthesia, and alert the anesthesiologist to the need to make changes to the concentration levels of the anesthesia. Although there are variations in the P100 latency, amplitude and morphology among individual patients, it is proposed that during surgery each patient's P100 can be measured prior to administering anesthesia to obtain a control level. Moreover, monitoring the visual pathways will provide a much more accurate measurement of awareness than does generic cerebral cortex activity, because the cortex controls a number of different functions which may or may not be affected by the anesthesia depending on the patient whereas visual function is fairly uniformly impacted by loss of consciousness.

In summary, using the monitor of the current invention awareness under anesthesia can be monitored in real-time, and an alert signaled should the awareness of the patient change thereby allowing the anesthesiologist the opportunity to make adjustments to the concentration of anesthesia being administered.

Example 3

VEP Curve Analysis

In another embodiment of the invention, a more sophisticated measurement of optic nerve function is proposed. In this embodiment, not only the peaks, but the entire waveform of the VEP of the patient is analyzed in accordance with novel techniques to determine subtle shifts in the function of the optic nerve, and by proxy the awareness level or risk of POVL of the patient. This technique will be discussed in reference to FIG. 12, which provides a plot of a normal flash VEP.

Figure 12:
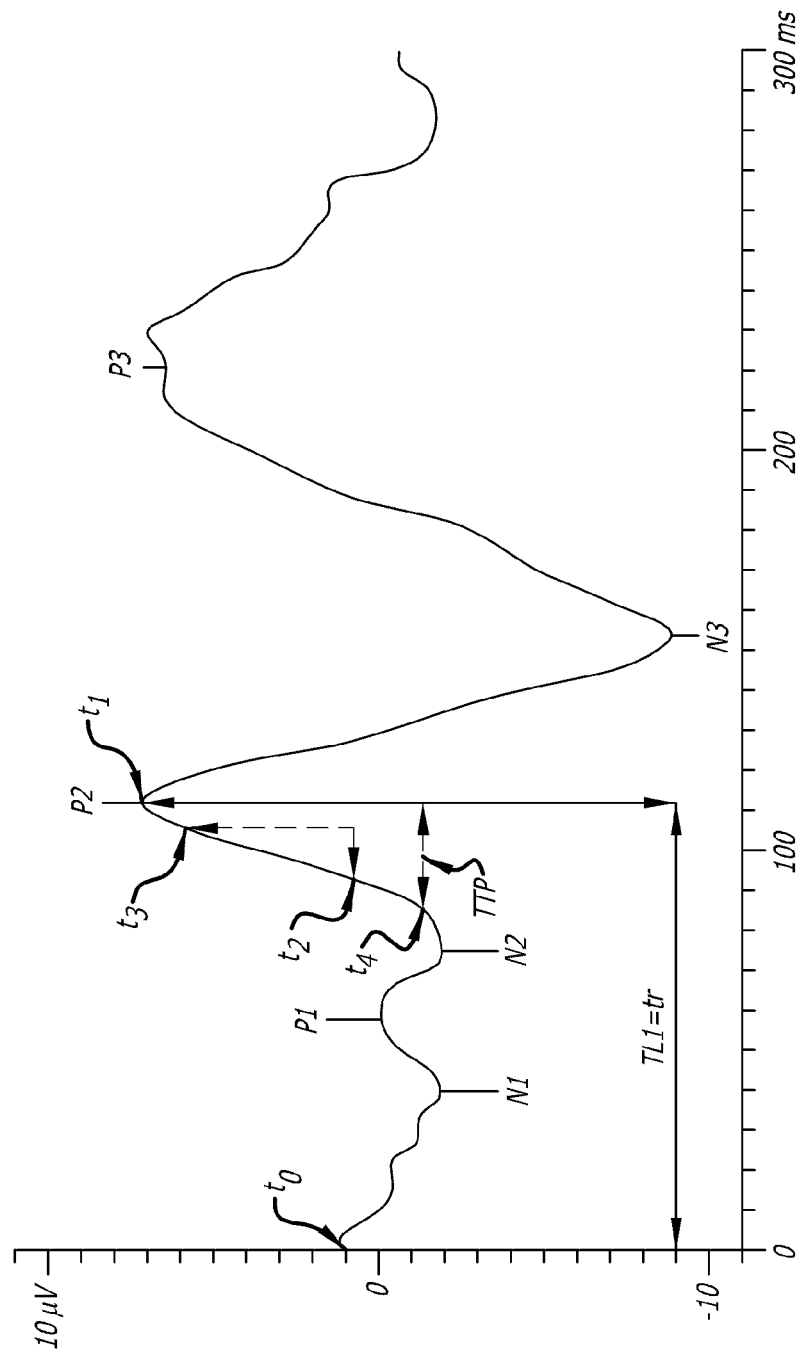
FIG. 12 provides a normal flash VEP waveform along with labels for important components of the VEP waveform.

In prior art studies that have used VEPs to examine the effects of anesthesia on a patient only the location and size of peaks has been examined. (See, e.g., Freye, E., *Cerebral Monitoring In The Operating Room And The Intensive Care Unit*, reprinted from J. Clinical Monitoring and Computing, 9:1-2 (2005), the disclosure of which is incorporated herein by reference.) However, as shown in FIG. 12, a VEP curve can be broken into many different parts, all of which are defined below.
- Latency 1 (TL1): Is defined herein as the temporal interval in milliseconds (ms) between the onset of stimulation ($t_0$) and the absolute manitude of the second evoked potential (EVP2) P2 (P2, µV) given as $t_1$ (ms).
- Evoked Potential 2 (EVP2): Is defined herein as the second and largest maximum visual evoked potential after photopic stimulation at $t_0$.
- P2: Is defined herein as the vertical distance between the maximum value of the upslope of EVP2, to a point corresponding in microvolts (µV) to the nadir (N3) of EVP2, the measurement of which is P2 (µV) minus N3 (µV), i.e., P2−N3 in µV.
- N3: Is defined as the nadir of the downslope of EVP2 (µV).
- Peak Forward Upslope Of EVP2 ($\delta(EVP2)/\delta t_{max}$): Is defined herein as the maximum upslope, or peak first time-derivative ($\delta/\delta t$) of EVP2, is found by extrapolating a line 15% above the baseline on the upslope at temporal interval $t_2$ (ms) to a point 10% below P2 on said upslope at temporal interval $t_3$ (ms) and dividing the magnitude in μV between the 15% and 10% points by the temporal interval ($t_3$ minus $t_2$) separating the said landmarks in ms, in accordance with the equation below.

$$\delta(EVP2)/\delta t_{max} = \mu V/ms \qquad (EQ. 1)$$

Mean Slope of EVP2 ($\delta(EVP2)/\delta t_{mean}$): Is defined herein as the quotient of P2 and the temporal interval occurring between the onset of the upslope of EVP2 and P2 ($t_4$), said interval occurring after N2, namely, the temporal point at onset of EVP2 being $t_4$, said temporal interval being TL1 (ms) minus $t_4$ (ms) (i.e., TL1−$t_4$), or, alternatively, the temporal interval of $t_1$ minus $t_4$ ($t_1$−$t_4$), this being Δt, said interval being the time to peak (TTP) or rise time from $t_4$ to $t_1$, the mean slope thus being P2 divided by TTP (i.e., P2/TTP), or, alternatively P2/Δt, given as μV/ms.

Awareness Index (AI): Is defined herein as a dimensional or dimensionless linear or non-linear function which approximates the level of cortical occipital lobe electrical activity and optic nerve conduction of VEPs. The AI may be used to determine the depth of general anesthesia, awareness under anesthesia and prevention of optic nerve dysfunction and blindness, that is, blindness caused by posterior ischemic optic neuropathy (PION).

By observing the change in the shape of the curve over time, it is possible to obtain information about the function of the optic nerve and in turn the effect anesthesia is having on the patient. It has been discovered that by monitoring specific features and combinations of features of VEP curve profiles it is possible to obtain much more nuanced information about the level of function of the optic nerve. The current invention proposes a number of different mathematical methodologies for analyzing these curves:

In a first embodiment (AI-1), the VEP curve is analyzed in accordance with the following equation:

$$AI\text{-}1 = P2/TL1 \text{ in } (\mu V/ms) \qquad (EQ. 2)$$

In a second embodiment (AI-2), the VEP curve is analyzed in accordance with the following equation:

$$AI\text{-}2 = (AI\text{-}1)^n \text{ in } (\mu V/ms) \qquad (EQ. 3)$$

where n is an exponent between 0.333 and 3, and preferably is between 0.5 and 2.

In a third embodiment (AI-3), the VEP curve is analyzed in accordance with the following equation:

$$AI\text{-}3 = (P2)^x/(TL1)^y \text{ in } (\mu V/ms) \qquad (EQ. 4)$$

where x and y are exponents between 0.333 and 3 and preferably between 0.5 and 2.

In a fourth embodiment (AI-4), the VEP curve is analyzed in accordance with the following equation:

$$AI\text{-}4 = (AI\text{-}3)^n \text{ in } (\mu V/ms) \qquad (EQ. 5)$$

where n is an exponent between 0.333 and 3, and preferably between 0.5 and 2.

In a fifth embodiment (AI-5), the VEP curve is analyzed in accordance with the following equation:

$$AI\text{-}5 = (\delta(EVP2)/\delta t_{max})/TL1 \text{ in } (\mu V/ms) \qquad (EQ. 6)$$

In a sixth embodiment (AI-6), the VEP curve is analyzed in accordance with the following equation:

$$AI\text{-}6 = (\delta(EVP2)/\delta t_{max})^x/(TL1)^y \text{ in } (\mu V/ms) \qquad (EQ. 7)$$

where x and y are exponents between 0.333 and 3, and preferably between 0.5 and 2.

In a seventh embodiment (AI-7), the VEP curve is analyzed in accordance with the following equation:

$$AI\text{-}7 = AI\text{-}6^n \text{ in } (\mu V/ms) \qquad (EQ. 8)$$

where n is an exponent between 0.333 and 3 and preferably between 0.5 and 2.

In an eight embodiment (AI-8), the VEP curve is analyzed in accordance with the following equation:

$$AI\text{-}8 = (\delta(EVP2)/\delta t_{mean})/TL1 \text{ in } (\mu V/ms) \qquad (EQ. 9)$$

In a ninth embodiment (AI-9), the VEP curve is analyzed in accordance with the following equation:

$$AI\text{-}9 = (\delta(EVP2)/\delta t_{mean})^x/(TL1)^y \text{ in } (\mu V/ms) \qquad (EQ. 10)$$

where x and y are exponents between 0.333 and 3, and preferably between 0.5 and 2.

In a tenth embodiment (AI-10), the VEP curve is analyzed in accordance with the following equation:

$$AI\text{-}10 = (\delta(EVP2)/\delta t_{mean})^x/(t_1^y/P2^z)^m \text{ in } (\mu V/ms) \qquad (EQ. 11)$$

where x, y, z and m are exponents between 0.333 and 3, and preferably between 0.5 and 2.

In an eleventh embodiment (AI-11), the VEP curve is analyzed in accordance with the following equation:

$$AI\text{-}11 = AI\text{-}10^n \text{ in } (\mu V/ms) \qquad (EQ. 12)$$

where n is an exponent between 0.333 and 3, and preferably between 0.5 and 2.

In a twelfth embodiment (AI-12), the VEP curve is analyzed in accordance with the following equation:

$$AI\text{-}12 = \delta(EVP2)/\delta t_{max}/t_1/P2 \text{ in } (\mu V^2/ms^2) \qquad (EQ. 13)$$

In a thirteenth embodiment (AI-13), the VEP curve is analyzed in accordance with the following equation:

$$AI\text{-}13 = (\delta(EVP2)/\delta t_{max})^x/t_1^y/P2^z \text{ in } (\mu V^2/ms^2) \qquad (EQ. 14)$$

where x, y and z are exponents between 0.333 and 3, and preferably between 0.5 and 2.

In a fourteenth embodiment (AI-14), the VEP curve is analyzed in accordance with the following equation:

$$AI\text{-}14 = (\delta(EVP2)/\delta t_{mean})^x/(t_1^y/P2^z)^m \text{ in } (\mu V^2/ms^2) \qquad (EQ. 15)$$

where x, y, z and m are exponents between 0.333 and 3, and preferably between 0.5 and 2.

In a fifteenth embodiment (AI-15), the VEP curve is analyzed in accordance with the following equation:

$$AI\text{-}15 = AI\text{-}14^n \text{ in } (\mu V/ms) \qquad (EQ. 16)$$

where n is an exponent between 0.333 and 3, and preferably between 0.5 and 2.

In a sixteenth embodiment (AI-16), the VEP curve is analyzed in accordance with the following equation:

$$AI\text{-}16 = (\delta(EVP2)/\delta t_{max})^x/(t_1^y/P2^z)^m \text{ in } (\mu V^2/ms^2) \qquad (EQ. 17)$$

where x, y, z and m are exponents between 0.333 and 3, and preferably between 0.5 and 2.

In a seventeenth embodiment (AI-17), the VEP curve is analyzed in accordance with the following equation:

$$AI\text{-}17 = AI\text{-}16^n \text{ in } (\mu V/ms) \qquad (EQ. 18)$$

where n is an exponent between 0.333 and 3, and preferably between 0.5 and 2.

In a eighteenth embodiment AI-18, each equation, i.e. dynamic equations AI-1 through AI-17, measured during the course of anesthesia and surgery, can be divided by a static control value CV, defined as each of the respective equations, 1 through 17, measured at the time of the onset of the study and before induction of anesthesia, the units of said quotient being a dimensionless index (AI-D). Therefore, the VEP curve is analyzed by the following equation(s):

$$AI\text{-}D = ((AI\text{-}1) \cdot (AI\text{-}17)) / (CV(AI\text{-}1) \cdot CV(AI\text{-}17)) \quad (\text{EQ. 19})$$

where AI-D is dimensionless, wherein the respective AI-Ds constitute the preferred embodiments of the method.

While under anesthesia the VEP curves of a patient are monitored and analyzed in accordance using one of the above methodologies. First, the curve is calibrated. To calibrate the absolute value of P2 ($\mu$V) may be implemented as measured prior to anesthesia, or, alternatively, a calibrated value of P2 can be made to equal P2 at a pre-determined age. In summary, by monitoring the values produced by the equations AI-1 through AI-18 it is possible to determine the level of anesthesia awareness or optic nerve injury, especially to the posterior portion of the optic nerve, which is the portion of the optic nerve that is most vulnerable in the prone (face down) or sitting positions.

CONCLUSION

In summary, the current invention is directed to a method and apparatus for monitoring optic function. The two basic principles are: (1) monitoring VEPs for neural function; and (2) monitoring at least one additional parameter of optic function such as intraocular pressure, blood flow or location of the eye to provide a multi-variable optic function monitor. The invention is proposed for use in particular to diagnose and potentially prevent the incidence of POVL and anaesthesia awareness in patients during medical procedures.

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A method of monitoring optic function comprising:
    providing at least one sensor and at least one visual evoked potential stimulator;
    disposing the at least one sensor and at least one visual evoked potential stimulator in stimulating relation with at least one eye of a patient, and the at least one sensor in monitoring relation with the patient;
    activating the stimulator to stimulate at least two portions of the at least one eye selected from the group consisting of the optic nerve, optic chiasma and the optic cortex to produce signals, said signals forming a visual evoked potential, the visual evoked potential being characterized by a waveform;
    collecting the waveform of the visual evoked potential in the at least one sensor;
    providing a data processor in signal communication with the at least one sensor to collect the waveform from the at least one sensor; and
    processing the measured waveform in the data processor such that changes in the waveform of the visual evoked potential over time are monitored for an adverse change in optic function to provide a real-time gauge of the health of the optic nerve of the patient, wherein the processing includes an analysis of at least the temporal interval (TL1) between the onset of stimulation ($t_0$) and the absolute magnitude of the second measured maximum visual evoked potential (EVP2) after stimulation, and at least one aspect of the waveform of EVP2 selected from the group consisting of the vertical distance (P2) between the maximum value of the upslope of EVP2 to the nadir (N3) of the EVP2, the peak first time-derivative of EVP2, the mean slope of EVP2, and combinations thereof.

2. The method of claim 1, wherein the stimulating and monitoring of the function of at least two portions of the eye includes producing a visual evoked potential in the nasal and temporal halves of the optic nerve.

3. The method of claim 1, wherein the stimulating and monitoring the function of the eye includes positioning at least two sensors and two visual evoked potential stimulators proximate to the eye.

4. The method of claim 1, wherein the at least one stimulator is a light emitting diode.

5. The method of claim 1, further comprising providing at least one pressure sensor and disposing said at least one pressure sensor in monitoring relation with the at least one eye for measuring the intraocular pressure of the at least one eye and evaluating the intraocular pressure for an adverse change in optic function of the patient.

6. The method of claim 5, wherein the at least one pressure sensor is a tonometer.

7. The method of claim 1, further comprising providing at least one blood flow sensor and disposing said at least one blow flow sensor in monitoring relation with the at least one eye for measuring one of either the retinal or the optic blood flow within the at least one eye and evaluating the one of either the retinal or optic blood flow for an adverse change in optic function of the patient.

8. The method of claim 7, wherein the blood flow sensor is selected from one of either a near-infrared spectrometer or a laser Doppler velocimeter.

9. The method of claim 1, further comprising placing a location sensor proximate to said eye; and
    monitoring said location sensor to determine the placement of said eye in relation to the eye socket.

10. The method of claim 9, wherein said location sensor further comprises a pressure transducer such that the location of the eye may be adjusted based on an output from the location sensor.

11. The method of claim 1, wherein the adverse change is one of either perioperative vision loss (POVL) or anesthesia awareness.

12. The method of claim 1, wherein the processing includes producing an evaluation number from the waveform of the VEP, said evaluation number being indicative of at least the level of optic function.

13. The method of claim 1, further comprising computing an anesthesia evaluation number from the VEP waveform in accordance with an equation selected from the group consisting of:
    P2/TL1, where P2 is the vertical distance between the maximum value of the upslope of a second and largest maximum visual evoked potential (EVP2) measured by the waveform to the nadir (N3) of the EVP2, and TL1 is the temporal interval between the onset of stimulation ($t_0$) and the absolute magnitude of the second evoked potential (EVP2);
    $(P2/TL1)^n$, wherein n is an exponent between 0.333 and 3;
    $(P2)^x/(TL1)^y$, where P2 is the vertical distance between the maximum value of the upslope of a second and largest maximum visual evoked potential (EVP2) measured by the waveform to the nadir (N3) of the EVP2, and TL1 is the temporal interval between the onset of stimulation ($t_0$) and the absolute magnitude of the EVP2, and wherein x and v are an exponents between 0.333 and 3;

$((P2)^x/(TL1)^y)^n$ where n is an exponent between 0.333 and 3;

$((P2)^x/(TL1)^y)^n$ where n is an exponent between 0.5 and 2;

$(\delta(EVP2)/\delta_{max})/TL1$, where (EVP2) is a second and largest maximum visual evoked potential, $\delta(EVP2)/\delta t_{max}$ is the peak forward upslope of EVP2, and TL1 is the temporal interval between the onset of stimulation ($t_0$) and the absolute magnitude of EVP2;

$(\delta(EVP2)/\delta t_{max})^x/(TL1)^y$, where (EVP2) is a second and largest maximum visual evoked potential, $\delta(EVP2)/\delta t_{max}$ is the peak forward upslope of EVP2, TL1 is the temporal interval between the onset of stimulation ($t_0$) and the absolute magnitude of EVP2, and wherein x and y are an exponents between 0.333 and 3;

$((\delta(EVP2)/\delta t_{max})^x/(TL1)^y)^n$ where n is an exponent between 0.333 and 3;

$(\delta(EVP2)/\delta t_{mean})/TL1$, where (EVP2) is a second and largest maximum visual evoked potential, $\delta(EVP2)/\delta t_{mean}$ is the mean sloe of EVP2 and P2, and TL1 is the temporal interval between the onset of stimulation ($t_0$) and the absolute magnitude of EVP2, and where P2 is the vertical distance between the maximum value of the upslope of a second and largest maximum visual evoked potential (EVP2) measured by the waveform to the nadir (N3) of the EVP2;

$(\delta(EVP2)/\delta t_{mean})^x/(TL1)^y$, where (EVP2) is a second and largest maximum visual evoked potential, $(\delta(EVP2)/\delta t_{mean}$ is the mean sloe of EVP2 and P2, TL1 is the temporal interval between the onset of stimulation ($t_0$) and the absolute maqnitude of EVP2, and wherein x and y are an exponents between 0.333 and 3, and where P2 is the vertical distance between the maximum value of the upslope of a second and largest maximum visual evoked potential (EVP2) measured by the waveform to the nadir (N3) of the EVP2;

$(\delta(EVP2)/\delta t_{mean})^x/(t_1^y/P2^z)^m$ in (μV/ms), where (EVP2) is a second and largest maximum visual evoked potential, $\delta(EVP2)/\delta t_{mean}$ is the quotient of P2 and the temporal interval occurring between the onset of the upslope of EVP2 and P2, $t_1$ is the absolute magnitude of EVP2, P2 is the vertical distance between the maximum value of the upslope of a second and largest maximum visual evoked potential (EVP2) measured by the waveform to the nadir (N3) of the EVP2, and wherein x and v are an exponents between 0.333 and 3;

$((\delta(EVP2)/\delta t_{mean})^x/(t_1^y/P2^z)^m)^n$ where n is an exponent between 0.333 and 3;

$\delta(EVP2)/\delta t_{max}/t_1/P2$ in (μV/ms), where(EVP2)is a second and largest maximum visual evoked potential, $\delta(EVP2/\delta t_{max}$ is the peak forward upslope of EVP2, $t_1$ is the absolute magnitude of EVP2, and P2 is the vertical distance between the maximum value of the upslope of a second and larqest maximum visual evoked potential (EVP2) measured by the waveform to the nadir (N3) of the EVP2;

$\delta(EVP2)/\delta t_{max}/t_1/P2$ in (μV/ms), where (EVP2) is a second and largest maximum visual evoked potential, $t_{max}$ $\delta(EVP2)/\delta t_{max}$ is the peak forward upslope of EVP2, $t_1$ is the absolute magnitude of EVP2, P2 is the vertical distance between the maximum value of the upslope of a second and largest maximum visual evoked potential (EVP2) measured by the waveform to the nadir (N3) of the EVP2, and wherein x, y and z are an exponents between 0.333 and 3;

$(\delta(EVP2)/\delta t_{mean})^x/(t_1^y/P2^z)^m$ in (μV/ms), where (EVP2) is a second and largest maximum visual evoked potential, $\delta(EVP2)/\delta t_{mean}$ is the mean slope of EVP2 and P2, $t_1$ is the absolute magnitude of EVP2, P2 is the vertical distance between the maximum value of the upslope of a second and largest maximum visual evoked potential (EVP2) measured by the waveform to the nadir (N3) of the EVP2, and wherein x, y, z and m are an exponents between 0.333 and 3;

$((\delta(EVP2)/\delta t_{mean})^x/(t_1^y/P2^z)^m)^n$ where n is an exponent between 0.333 and 3;

$(\delta(EVP2)/\delta t_{max})^x/(t_1^y/P2^z)^m$ in (μV/ms), where n (EVP2) is a second and largest maximum visual evoked potential $\delta(EVP2)/\delta t_{max}$ is the peak forward upslope of EVP2, $t_1$ is the absolute magnitude of EVP2), P2 is the vertical distance between the maximum value of the upslope of a second and largest maximum visual evoked potential (EVP2) measured by the waveform to the nadir (N3) of the EVP2, and wherein x, y, z and m are an exponents between 0.333 and 3; and $((\delta(EVP2)/\delta t_{max})^x/(t_1^y/P2^z)^m)^n$ where n is an exponent between 0.333 and 3.

14. The method as in claim 13, further comprising computing a dimensionless anesthesia evaluation index, obtained by dividing the anesthesia evaluation number by a static control value defined as the value of the anesthesia evaluation number measured at a time before the induction of anesthesia.

15. The method of claim 1, further comprising computing two anesthesia evaluation numbers from the VEP waveform in accordance with the equation, $(P2)^x/(TL1)^y$, where P2 is the vertical distance between the maximum value of the upslope of a second and largest maximum visual evoked potential (EVP2) measured by the waveform to the nadir (N3) of the EVP2, and TL1 is the temporal interval between the onset of stimulation ($t_0$) and the absolute magnitude of the EVP2, and wherein x and y are an exponents between 0.333 and 3;

computing a third anesthesia evaluation number according to the equation $((P2)^x/(TL1)^y)^n$ where n is an exponent between 0.333 and 3; and further comprising computing a dimensionless anesthesia evaluation index obtained by dividing the third anesthesia evaluation number by a static control value defined as the value of the third anesthesia evaluation number measured at a time before the induction of anesthesia.

16. The method as in one of claim 13, further comprising calibrating the anesthesia evaluation number by measuring the anesthesia evaluation number prior to the administration of an anesthesia.

* * * * *